US011638698B2

(12) United States Patent
Szto et al.

(10) Patent No.: US 11,638,698 B2
(45) Date of Patent: May 2, 2023

(54) LIQUID CRYSTALLINE DOSAGE FORM FOR ADMINISTERING A STATIN

(71) Applicant: Zeenar Enterprises Pty Ltd, Brighton (AU)

(72) Inventors: Gregory Yu Foo Szto, Melbourne (AU); Tomer Madmon, Melbourne (AU); David Kannar, Melbourne (AU)

(73) Assignee: Zeenar Enterprises Pty Ltd, Brighton (AU)

( * ) Notice: Subject to any disclaimer, the term of this patent is extended or adjusted under 35 U.S.C. 154(b) by 66 days.

(21) Appl. No.: 16/606,149

(22) PCT Filed: Apr. 20, 2018

(86) PCT No.: PCT/AU2018/050367
§ 371 (c)(1),
(2) Date: Oct. 17, 2019

(87) PCT Pub. No.: WO2018/191794
PCT Pub. Date: Oct. 25, 2018

(65) Prior Publication Data
US 2021/0145752 A1    May 20, 2021

(30) Foreign Application Priority Data

Apr. 20, 2017  (AU) ................................ 2017901444
Dec. 20, 2017  (AU) ................................ 2017905102
Mar. 9, 2018   (AU) ................................ 2018900788

(51) Int. Cl.
A61K 9/20    (2006.01)
A61K 9/00    (2006.01)
(Continued)

(52) U.S. Cl.
CPC .......... A61K 9/2013 (2013.01); A61K 9/0056 (2013.01); A61K 31/40 (2013.01); A61K 31/505 (2013.01); A61P 3/06 (2018.01)

(58) Field of Classification Search
CPC .... A61K 9/2013; A61K 9/0056; A61K 31/40; A61K 31/505; A61P 3/06
See application file for complete search history.

(56) References Cited

U.S. PATENT DOCUMENTS 4,681,893 A  *  7/1987  Roth .................... C07D 405/06
                                                      514/422
2005/0196438 A1    9/2005  Wang et al.
(Continued)

FOREIGN PATENT DOCUMENTS

EP        2826465 A1      1/2015
WO    WO-97/13528 A1      4/1997
(Continued)

OTHER PUBLICATIONS

Pfizer, "Lipitor", Jun. 2009. (Year: 2009).*
(Continued)

*Primary Examiner* — Jianfeng Song
(74) *Attorney, Agent, or Firm* — Clark & Elbing LLP

(57) ABSTRACT

A composition including an amphiphilic compound capable of self-assembling into liquid crystalline particles and a statin for systemic administration via oral mucosa. A method of lowering blood cholesterol levels in a subject comprising administering the self-assembling liquid crystalline particles and statin via oral mucosa. Preferred dosage forms result in prolonged release of the statin.

20 Claims, 9 Drawing Sheets

(51) Int. Cl.
*A61K 31/40* (2006.01)
*A61P 3/06* (2006.01)
*A61K 31/505* (2006.01)

(56) References Cited

U.S. PATENT DOCUMENTS

| | | |
|---|---|---|
| 2008/0031947 A1 | 2/2008 | Hamed et al. |
| 2010/0010101 A1 | 1/2010 | Cherukuri |
| 2013/0034538 A1 | 2/2013 | Garti et al. |
| 2016/0081996 A1 | 3/2016 | Mulet et al. |

FOREIGN PATENT DOCUMENTS

| | | | |
|---|---|---|---|
| WO | WO-2005/117830 A1 | 12/2005 | |
| WO | WO-2006/013369 A2 | 2/2006 | |
| WO | WO-2007/020079 A2 | 2/2007 | |
| WO | WO-2007/031801 A1 | 3/2007 | |
| WO | WO-2008/002529 A2 | 1/2008 | |
| WO | WO-2009/086046 A1 | 7/2009 | |
| WO | WO-2013/088161 A1 | 6/2013 | |
| WO | WO-2013/183062 A2 | 12/2013 | |
| WO | WO-2014/179845 A1 | 11/2014 | |
| WO | WO-2014179845 A1 * | 11/2014 | ........... A61K 31/201 |
| WO | WO-2015/132660 A1 | 9/2015 | |
| WO | WO-2015/176008 A1 | 11/2015 | |
| WO | WO-2015/189726 A1 | 12/2015 | |
| WO | WO-2016/053092 A1 | 4/2016 | |
| WO | WO-2016/069871 A1 | 5/2016 | |
| WO | WO-2017/017679 A1 | 2/2017 | |
| WO | WO-2018/191792 A1 | 10/2018 | |
| WO | WO-2018/191793 A1 | 10/2018 | |
| WO | WO-2020/082137 A1 | 4/2020 | |

OTHER PUBLICATIONS

Davies, "A quantitative kinetic theory of emulsion type. I. Physical chemistry of the emulsifying agent," *Gas/Liquid and Liquid/Liquid Interfaces: Proceedings of the International Congress of Surface Activity*, 426-38 (1957).

Du et al., "A novel approach to enhance the mucoadhesion of lipid drug nanocarriers for improved drug delivery to the buccal mucosa," Int J Pharm. 471 (1-2):358-65 (2014).

Gabr et al., "Hexagonal liquid crystalline nanodispersions proven superiority for enhanced oral delivery of rosuvastatin: in vitro characterization and in vivo pharmacokinetic study," J Pharm Sci. 106(10):3103-12 (2017).

Guo et al., "Lyotropic liquid crystal systems in drug delivery," Drug Discov Today. 15(23-24):1032-40 (2010).

International Search Report for International Patent Application No. PCT/AU2018/050367, dated Jun. 28, 2018 (9 pages).

Lai et al., "Glyceryl monooleate/poloxamer 407 cubic nanoparticles as oral drug delivery systems: I. In vitro evaluation and enhanced oral bioavailability of the poorly water-soluble drug simvastatin," AAPS PharmSciTech. 10(3):960-6 (2009).

Moebus et al., "Cubic phase-forming dry powders for controlled drug delivery on mucosal surfaces," J Control Release. 157(2): 206-15 (2012).

Pan et al., "Nanostructed cubosomes as advanced drug delivery system," Curr Pharm Des. 19(35):6290-7 (2013).

Puratchikody et al., "Buccal drug delivery: past, present and future—a review," Int J Drug Deliv. 3(2):171-84 (2011).

Souza et al., "Mucoadhesive system formed by liquid crystals for buccal administration of poly(hexamethylene biguanide) hydrochloride," J Pharm Sci. 103(12):3914-23 (2014).

Milak et al., "Glycerol monooleate liquid crystalline phases used in drug delivery systems," Int J Pharm. 478(2):569-87 (2015).

Shah et al., "Spray dried glyceryl monooleate-magnesium trisilicate dry powder as cubic phase precursor," Int J Pharm. 323(1-2):18-26 (2006).

\* cited by examiner

LIQUID CRYSTALLINE DOSAGE FORM FOR ADMINISTERING A STATIN

FIELD OF THE INVENTION

The present invention relates to methods of lowering blood cholesterol in a subject, in particular, the method comprises administration of a statin via the oral mucosa. The invention also relates to dosage forms capable of administering statins via oral mucosa.

BACKGROUND OF THE INVENTION

Oral drug delivery is currently the most popular and convenient form of drug administration. Orally delivered drugs must however survive stomach acid and resist enzymatic attack before being absorbed across the gastrointestinal (GI) membrane. The functions of the GI tract are digestion and absorption of food and other nutrients but these functions can interfere with drug absorption. The pH of the GI tract contents and presence of enzymes, foodstuffs, bile salts, fat and microbial flora can all interfere with drug absorption. Consequently, the amount of drug required to be administered orally can be significantly larger than the amount of drug made systemically available by this method of delivery. In addition, delivery of many drugs by this method results in gastrointestinal side effects.

Statins are a class of medications prescribed for reducing low-density lipoproteins (LDL) or "bad" cholesterol in circulating blood, which are known to cause heart disease. Increasing high-density lipoprotein or HDL is also desirable, but statins do not typically have a significant effect on HDL.

Statins are an example of drugs that, when taken orally, have a high incidence of side effects. In 2012, a large US survey reported that up to 12% of 10,318 patients prescribed statins for reducing low density lipoproteins (LDL), discontinued medication within 1 year from treatment initiation because of side effects (see Cohen J. D. et al., 2012, *International Journal of Lipidology*). Side effects include gastrointestinal discomfort, rash, headache, nephrotoxicity, hepatotoxicity and muscle related complications such as muscle pain (ie myalgia), muscle inflammation (myositis) and/or myopathy (a muscle disease). Statin intolerance occurs when a patient is unable to continue to use a statin, either because of the development of a side effect or because of evidence on a blood test that certain markers of liver function or muscle function (ie creatine kinase) are sufficiently abnormal to cause concern. Common forms of statin intolerance include statin-induced myalgia and statin-induced myopathy. In patients reporting concerns or experiencing side effects, statin dose is normally reduced and other therapies introduced, especially for those at high risk of heart disease. However, this reduced treatment does not have ideal efficacy. There is a need for effective LDL lowering therapies with a low frequency, lower severity of side effects and/or different side effects to provide options for patients that have difficulties with the currently available oral statin medications.

A drug can be delivered intravenously or by injection however this form of administration is undesirable, particularly where frequent dosing is required, because many patients are not able to self-administer this type of medication and, at certain frequencies of dosing, administration by a medical professional is prohibitively expensive and/or inconvenient.

Delivery via the oral mucosa is one way to avoid gastrointestinal side effects. However, delivery via oral mucosa can be so rapid that this method can also be responsible for significant side effects, that is, side effects related to rapid increases in blood levels of the drug rather than side effects related to gastrointestinal irritation.

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

SUMMARY OF THE INVENTION

In one aspect, the present invention provides a method of lowering blood cholesterol levels in a subject in need thereof comprising administering a composition to the oral mucosa of the subject, wherein the composition comprises an amphiphilic compound capable of self-assembling into a liquid crystalline phase and a statin compound, and wherein the statin compound is systemically administered via oral mucosa. The advantage of systemic administration of a statin via oral mucosa is that drug delivery is not via the gastrointestinal tract. Therefore, first pass metabolism by the liver is avoided and efficacious blood levels of the statin can be achieved with a lower dose. Delivery via oral mucosa also avoids the gastrointestinal side effects that limit the use of statins. The formation of the liquid crystalline phase prolongs absorbance of the statin compared to the rapid absorption usual for administration via oral mucosa.

Without being bound by any theory or mode of action, it is believed that prolonging release of the statin has the advantage of minimising the blood concentration of statin. Without being bound by any theory or mode of action, it is believed that this is advantageous as some side effects are proportional to the maximum blood concentration. If the above theory proves to be correct then it is possible that adapting from oral delivery of a statin to delivery of a statin via the oral mucosa could minimise side effects while still maintaining acceptable efficacy.

The administration via oral mucosa is optionally via the buccal or sublingual administration.

Methods of the invention include methods of treating or preventing the development of dyslipidaemia, preferably hyperlipidaemia, cardiovascular disease and/or atherosclerosis. Alternatively, the method treats subjects at risk of developing dyslipidaemia, preferably hyperlipidaemia, cardiovascular disease and/or atherosclerosis. Alternatively, the method treats or prevents statin-intolerance, preferably statin-induced myalgia, statin-induced myositis and/or statin-induced myopathy. Where the method treats of prevents statin-intolerance it is preferred that the method also reduces the total cholesterol. Where a subject has been taking traditional statin medication, such as, Crestor or Lipitor, it is preferred that the method of the present invention further reduces the subject's total cholesterol, maintains the subject's reduction in total cholesterol or minimises the subject's increase in total cholesterol.

Optionally, the subject is identified as in need of blood cholesterol lowering. The subject optionally has dyslipidaemia, preferably hyperlipidaemia, cardiovascular disease and/or atherosclerosis. Alternatively, the subject is at risk of developing dyslipidaemia, preferably hyperlipidaemia, cardiovascular disease and/or atherosclerosis.

Optionally, the subject is identified as in need of treatment for statin-intolerance, preferably statin-induced myalgia, statin-induced myositis and/or statin-induced myopathy.

When administered via oral mucosa, it is possible to use statins in lower doses than those conventionally used in oral dosage forms. The statin is optionally administered in methods of the invention a dose of 0.5 to 30 mg/day, 1 to 20 mg/day, 2 to 10 mg/day, 0.5 to 7 mg/day, 3 to 6 mg/day or 0.5 to 5 mg/day. Preferred methods comprise administration of 5 mg/day. The dose can be administered in either a single composition or multiple compositions. Multiple compositions can be administered at the same time or at different times of the day. In one option, administration is by a single dose in the morning. In another option, administration is by a single dose in the evening before bed. In a third option, administration is both in the morning and in the evening before bed. The composition is optionally administered daily, twice daily or on alternate days.

In some embodiments, the method results in a reduction in total cholesterol of about 15% to about 30%, about 17% to about 28% or about 20% to about 25%. Alternatively, the method results in a reduction in total cholesterol of about 15% to about 40%, about 20% to about 35% or about 25% to about 30%. In other embodiments, the method results in a reduction in LDL-C of about 25% to about 50%, about 27% to about 48% or about 30% to about 40%. Alternatively, the method results in a reduction in LDL-C of about 35% to about 45% or about 40% to about 45%. In further embodiments, the method results in the above reduction in total cholesterol and the above reduction in LDL-C. In some embodiments, the method results in an increase in HDL of up to about 5%, up to about 4%, up to about 3% or about 5%. Alternatively, the method results in an increase in HDL of up to about 8%, up to about 7% or up to about 6%. In other embodiments, the method may result in the above reduction in total cholesterol and the above increase in HDL, the above reduction in LDL-C and the above increase in HDL or the above reduction in total cholesterol, the above reduction in LDL-C and the above increase in HDL.

The method can result in the above reductions in total cholesterol and/or LDL-C and/or the above increase in HDL within 6 weeks, 4 weeks or 2 weeks of treatment. Alternatively, the above reductions in total cholesterol and/or LDL-C and/or the above increase in HDL within occur within 14 days, 10 days, 7 days, 5 days or 3 days of treatment.

The method of treating a person optionally comprises administration of a prolonged release dosage form. The prolonged release is optionally compared to an immediate release dosage form for delivery of an active ingredient via the oral mucosa or an immediate release oral tablet. The prolonged release optionally results in a sustained therapeutic effect. The delivery via the oral mucosa and/or the prolonged release optionally lessens the frequency or intensity of one or more side effects that occur with oral delivery and/or immediate release.

The maximum blood concentration of the active ingredient is optionally achieved over 30 minutes following administration of the ODT, over 45 minutes following administration of the ODT, over 1 hour following administration of the ODT, over 2 hours following administration of the ODT, over 3 hours following administration of the ODT, over 4 hours following administration of the ODT or over 5 hours following administration of the ODT. It will be understood that the time taken to maximum blood concentration can vary depending on the active ingredient used.

In some embodiments, the blood concentration following administration of the ODT is within 30% of the maximum blood concentration for 30 minutes, 1 hour, 90 minutes or 2 hours or more.

The amphiphilic compound is optionally present at an amount of about 1 to 20% w/w of the composition. In some embodiments the amount of amphiphilic compound is 3 to 10% w/w, 4 to 8% w/w, 4.5 to 7.5% w/w or 5 to 7% w/w. In preferred embodiments the amount of amphiphilic compound is about 5% w/w or about 7% w/w. Use of about 5% w/w of amphiphilic compound is preferred for formulations with an about 1:1 w/w ratio of amphiphilic compound and statin. Use of about 7% w/w of amphiphilic compound is preferred for formulations with an about 4:1 w/w ratio of amphiphilic compound and statin.

The amphiphilic compound is a compound that possesses both a hydrophilic portion and a hydrophobic portion and capable of self-assembling into liquid crystalline particles. The amphiphilic compound can also be a mixture of amphiphiles. Amphiphiles capable of self-assembly behaviour have been described in various publications, such as, for example, Drummond (2000). Examples of amphiphiles that are capable of self-assembly include, but are not limited to: surfactants, lipids, and block copolymers. More specifically, the amphiphilic compound is optionally selected from: fatty acids, fatty alcohols, acylglycerols, glycolipids, sphingolipids, phospholipids, cholesterol and mixtures thereof.

Optionally, the amphiphilic compound is non-ionic.

Hydrophilic-lipophilic balance (HLB) is a measure of the hydrophilicity/lipophilicity of an amphiphile. A HLB under 10 indicates lipid solubility and a HLB over 10 indicates water solubility. Optionally, the compound has a HLB of less than about 10, less than 8 or less than 6. Optionally, the HLB is greater than about 1. Optionally, the HLB is 0 to <10, or 1 to <10, 0 to <8, 1 to <8, 0 to <6 or 1 to <6.

The critical packing parameter (CPP) measures the relative volume of the head (hydrophilic portion) and tail (lipophilic portion) of a surfactant. The CPP indicates the type of liquid crystal likely to form when an amphiphilic compound is in solution at a level above its critical micelle concentration. A CPP of 1 means the surfactant is symmetrical. The CPP is the tail volume (V) divided by the sum of the effective head area (a) and the tail length (l) (ie CPP=V/(a.l)). An amphiphile with a CPP<1/3 is likely to form spherical micelles. An amphiphile with a CPP>1/3 but <1/2 is likely to form cylindrical micelles. An amphiphile with a CPP>1/2 but <1 is likely to form lamella micelles. An amphiphile with a CPP>1 is likely to form inversed spherical micelles. The amphiphilic compound of the invention optionally has a CPP>1/3, >1/2, or >1 at body temperature, atmospheric pressure and in water, pbs or saliva.

Optionally, the amphiphilic compound is a non-ionic amphiphile comprising a HLB of 0 to >10 and a CPP of >1/2. Optionally, the amphiphilic compound is a non-ionic amphiphile comprising a HLB of 1 to >8 and a CPP of >1.

In some embodiments the amphiphilic compound comprises Formula (I):

$$H\text{-}T \qquad (I)$$

wherein

H is selected from the group consisting of an ester, ether, anhydride, amide, amine, carbamide, glycerol, biuret, phenyl, pyridine or phosphate having at least 2 hydrogen bond forming functional groups; and T is selected form the group consisting of:
  (i) a single $C_{12}$ to $C_{18}$ alkyl, alkenyl and alkynyl terminally attached to H optionally comprising:
    a. one or more double bonds (preferably cis and at about C7 to C11); or
    b. three or more methyl branches (preferably isoprenoid branching);

and
(ii) two $C_{12}$ to $C_{18}$ alkyl, alkenyl and alkynyl both terminally attached to H. The ester and amide groups etc of H can be present in either orientation ie the ester could be —OC(O)-T or —C(O)O-T.

The ester and amide groups etc of H can be present in either orientation ie the ester could be —OC(O)-T or —C(O)O-T.

Optionally, the ester, ether, anhydride, amide, amine, carbamide, glycerol, biuret, phenyl, pyridine or phosphate forms part of, or is substituted with, a sugar (eg glucoside), xyloside (monomer or dimer) or $C_1$ to $C_4$ alkyl, alkenyl or alkynyl optionally with two to six hydroxyl, amine or methanol groups and attached at either a terminal or non-terminal carbon.

Optionally, H is selected from the group consisting of ester, ether, amine, amide or glycerol.

Optionally, H has 3 to 6 hydrogen bond forming groups.

Optionally, T has a molecular weight of at least >200 amu.

The amphiphilic compound is optionally selected from the group consisting of glycerol monooleate, glyceryl monolinoleate, glyceryl monooleyl ether, oleyl glycerate, monovaccenin, oleyl urea, linoleyl urea, phytanyl urea, hexahydrofarnesyl-urea, monooleain, phytantriol, glucose stearate, fructose stearate and combinations thereof.

In one embodiment, the amphiphilic compound is selected from a fatty acid comprising a 6 to 24 carbon chain, preferably a 12 to 24 carbon chain, more preferably a 16 to 20 carbon chain, most preferably an 18 carbon chain. The amphiphilic compound can also be a mixture of fatty acids. In a preferred embodiment, the amphiphilic compound is selected from one or more mono- and/or di-glycerides of fatty acids comprising a 6 to 24 carbon chain, preferably a 12 to 24 carbon chain, more preferably a 16 to 20 carbon chain, most preferably an 18 carbon chain. The carbon chain optionally has one or more double bonds such that it is unsaturated. One preferred class of amphiphilic compounds is glycerol monooleates (GMOs). The Handbook of Pharmaceutical Excipients lists GMO as having a HLB of 3.3. In a particularly preferred embodiment the amphiphilic compound is Myverol™18-99k (trade mark owned by Kerry Group Services Limited). Myverol™ is generally considered a GMO despite including some non-GMO amphiphiles. Myverol™ 18-99k is produced from the reaction of glycerol with canola (low erucic acid rapeseed) oil and contains a mixture of monoacylglycerols, diacylglycerols and glycerol. The compositional analysis of Myverol™ 18-99k is detailed in Clogston (Clogston 2000) wherein Myverol™18-99k was found to contain 82% monoacylglycerols (consisting of 86.6% monoolein (1-Oleoyl-rac-glycerol), 7.0% monostearin (1-Stearoyl-rac-glycerol), 3.5% monopalmitin (1-monohexadecanoyl-rac-glycerol), 0.9% monoarachidin (1-Arachidonoyl-glycerol) and 2.0% unidentified monoacylglycerols), 13.4% diacylglycerols (consisting of 7.4% 1,2-diacylglycerol and 6.0% 1,3-diacylglycerol) and 4.3% glycerol.

Another grade of GMO suitable for use in the present invention is comprised of about 90-100% monoglycerides (preferably about 95%), about 0-10% diglycerides (preferably about 4%) and about 0-2% triglycerides (preferably about 0.5%). It is preferred if this GMO has not less than 60% methyl oleate (preferably about 65%) and more preferred that the GMO also has not more than 35% methyl linoleate (preferably about 18-20%). The remaining fatty acid composition of the GMO is optionally not more than 12% methyl palmitate (preferably about 4%), not more than 6% methyl stearate (preferably about 2%), not more than 2% methyl linolenate, not more than 2% methyl arachidate, not more than 2% methyl eicosenate and not more than 6% free glycerine (preferably less than 1%).

Thus, in one embodiment the amphiphilic compound is a mixture of amphiphiles. Preferably, the amphiphilic compound contains a mixture of monoacylglycerols, diacylglycerols and glycerol. In particular, the mixture of amphiphiles is produced by reacting glycerol with canola oil. One suitable available amphiphilic compound contains 82% monoacylglycerols, 13.4% diacylglycerols and 4.3% glycerol. More particularly, the amphiphilic compound can contain:

82% monoacylglycerols consisting of 86.6% monoolein, 7.0% monostearin, 3.5% monopalmitin, 0.9% monoarachidin and 2.0% unidentified monoacylglycerols;

13.4% diacylglycerols consisting of 7.4% 1,2-diacylglycerol and 6.0% 1,3-diacylglycerol; and 4.3% glycerol.

In a further embodiment, the amphiphilic compound includes (i) a mixture of a mono- and/or di-glyceride of one or more fatty acids and (ii) one or more free fatty acids. Thus, the amphiphilic compound can include Myverol™ 18-99k and a fatty acid, such as oleic acid. In a further embodiment, the amphiphilic compound includes monoacylglycerol and oil.

In some embodiments, w/w ratio of amphiphilic compound to active ingredient is 10:1 to 1:100, 1:1 to 1:100, 10:1 to 1:1, 5:1 to 1:50, 1:1 to 1:25 or 1:1 to 1:10. Preferred ratios are about 1:1 to 7:1, about 1:1 to 4:1 or about 4:1 to 7:1. Alternatively, the w/w ratio of amphiphilic compound to active ingredient is about 1:1, about 4:1 or about 7:1.

The self-assembled particles are optionally selected from the following group: cubosomes, hexosomes, sponge particles and mixtures thereof, preferably cubosomes.

The self-assembled particles optionally form a bulk phase selected from the group consisting of micellar (normal and reversed), lamellar, hexagonal (normal and reversed), cubic (normal discrete, reversed discrete, reversed bicontinuous—including primitive, gyroid and diamond—and reversed discontinuous), and other 'intermediate phases' such as the ribbon, mesh, or non-cubic 'sponge' bicontinuous phases. See Israelachvili, J (1994) and Chang (1998) for more detail. In a preferred embodiment, the bulk phase is selected from cubic phase, hexagonal phase and mixtures thereof, preferably reversed bicontinuous cubic phase, preferably the diamond phase. Optionally, the bulk phase is lamellar phase. Optionally, the bulk phase is lamellar, reversed cubic or reversed hexagonal.

Without being bound by theory or mode of action, it is believed that the more complex the self-assembled particles and/or bulk phase, the slower the release of the active ingredient. Thus, the hexagonal and cubic, particularly diamond cubic, bulk phases are believed to result in the slowest release.

In some embodiments, the active ingredient is incorporated or dissolved within the self-assembled structure. Preferably, the active ingredient is non-covalently incorporated. The active ingredient is optionally in the form of a prodrug. In this embodiment, the active ingredient needs to be cleaved, for example by an enzyme or hydrolysis, either before or after absorption to form the active ingredient.

Suitable statins for the composition of the invention include, but are not limited to: atorvastatin, fluvastatin, lovastatin, mevastatin, pitavastatin, pravastatin, rosuvastatin, simvastatin and mixtures thereof. Statins used in the invention are optionally hydrophobic (ie lipophilic) but are preferably hydrophilic. Hydrophilic statins, including fluvastatin, pravastatin and rosuvastatin are less toxic than lipophilic statins, including atorvastatin, lovastatin and simvastatin. In a preferred embodiment, the pharmaceutical composition includes any one or more of fluvastatin, pravastatin and rosuvastatin. In particularly preferred embodiments of the invention the statin is rosuvastatin. It is preferred for the statin to be micronized.

It is preferred for the composition to adhere to the oral mucosa. Alternatively or in addition, the self-assembled structures formed upon contact with a hydrophilic solvent are preferred to adhere to oral mucosa. Optionally, the solvent is saliva or water.

In some embodiments of the present invention, the composition physically disintegrates into particles upon contact with a hydrophilic solvent (such as saliva). In some embodiments of the invention, when the composition disintegrates upon contact with a hydrophilic solvent the amphiphilic compound self-assembles into liquid crystalline particles that encapsulate or entrain the statin compound.

Optionally, when the composition is administered to the oral mucosa, the composition facilitates systemic administration of the statin compound across the oral mucosa.

In preferred embodiments, the composition of the invention is an oral disintegrating tablet (ODT). The ODT is suitable for administration to oral mucosa. An ODT suitable for administration to the oral mucosa comprises a statin, an amphiphile, a disintegrant and optionally a muccoadhesive. In some embodiments, disintegration occurs in 2 to 20 minutes, 2 to 15 minutes or 2 to 10 minutes. Alternatively, disintegration takes less than 120 seconds, 1 to 110 seconds, 10 to 90 seconds, 60 seconds or less, 30 seconds or less or 10 seconds or less. In other embodiments, disintegration takes 3 to 5 minutes, 5 to 10 minutes or 5 to 15 minutes. In some embodiments ODTs are formulated for speed of disintegration and others are formulated to enhance permeation of the mucosa. For example, an enhancer may be included to improve permeation but this could slow disintegration and stabilizing polymers such as polyethylene glycol could be avoided to speed disintegration. In muccoadhesive embodiments the muccoadhesive is optionally the same ingredient as the amphiphile. Some amphiphiles have muccoadhesive properties, for example, glycerol monooleate.

In preferred ODTs, the pharmaceutically acceptable disintegrant is present at an amount of about 1 to about 60% w/w of the ODT. In some embodiments the amount of pharmaceutically acceptable disintegrant is about 10 to about 50%, about 20 to about 60%, about 20 to about 50%, about 20 to about 40%, about 15 to about 40% w/w, about 20 to about 30% w/w, about 10 to about 20% w/w of the ODT. Alternatively, the ODT is prepared with low disintegrant content of about 1 to about 10% w/w of the ODT. Alternatively, the ODT does not contain disintegrant.

In some embodiments, the pharmaceutically acceptable disintegrant is selected from the group consisting of sodium starch glycolate, copovidone, crosslinked polyvinylpyrrolidone (crospovidone) or a derivative of crospovidone such as, crosslinked sodium carboxymethyl cellulose (croscarmellose sodium) sodium/calcium carboxymethylcellulose, sodium bicarbonate, microcrystalline cellulose, low-substituted hydroxypropylcellulose or sodium starch glycolate. Crospovidone can be added to the ODT independently or in the form of a blend such as Pharmaburst™, which contains 7-15% crospovidone.

Preferred compositions of the invention comprise two or more disintegrants. It is preferred if one of the two or more disintegrants is crospovidone. In some embodiments, the two or more disintegrants include both crospovidone and sorbitol copovidone. In some embodiments there are two disintegrants. These disintegrants are optionally crospovidone and copovidone or sodium starch glycolate and crospovidone.

Preferred compositions of the invention comprise three or more disintegrants. The three or more disintegrants are preferred to be crospovidone, copovidone and sodium starch glycolate.

Where the composition includes crospovidone, the crospovidone is preferred to be about 5 to about 45%, about 10 to about 45% w/w of the formulation, about 15 to about 35% w/w of the formulation or about 20 to about 25% w/w of the formulation. Where the formulation includes crospovidone, and sodium starch glycolate, the preferred amounts of crospovidone are as above and the preferred amount of sodium starch glycolate is about 3 to about 8% w/w or about 5% w/w of the formulation.

Some compositions include an enhancer. The use of polyethylene glycols (PEGs) has been described (WO2010144943) to improve absorption and speed (from slow to rapid) onset of action.

All embodiments of the composition of the invention optionally further comprise additional pharmaceutically acceptable excipients such as one or more filler, binder, glidant, lubricant, osmotic agent, sweetener and/or flavour.

Preferred ODTs are stable for at least 2 years, at least 1 year, at least 9 months, at least 6 months or at least 3 months. In some embodiments ODTs are stable at 25° C./60% relative humidity for at least 2 years, at least 1 year, at least 9 months, at least 6 months or at least 3 months and/or stable at 5° C. for at least 2 years, at least 1 year, at least 9 months, at least 6 months or at least 3 months, in particular, preferred ODTs retain about 90% or about 95% or more active ingredient following storage at either 25° C./60% relative humidity or 5° C. for at least 2 years, at least 1 year, at least 9 months or at least 6 months. Optionally, there is also no change in lactone or 5-oxo-rosuvastatin calcium levels following storage at 5° C. for at least 3, 6 or 9 months and/or less than 0.5% w/w lactone and less than 0.4% w/w 5-oxo-rosuvastatin calcium following storage at 25° C./60% relative humidity for at least 3 or 6 months.

The ODT optionally further include a second active ingredient. It is preferred for the active ingredient and optional second active ingredient to be micronized. The particle size of the active ingredient and optional second active ingredients is preferred to be about 10 μm.

The ODT according to the current invention can be prepared by spray drying, thermoplastic granulation, wet granulation or any of these processes followed by mixing with further ingredients. Preferred formulations are prepared by wet granulation.

The composition according to the current invention is optionally solid, liquid or semisolid. The composition is optionally dehydrated, freeze-dried, spray freeze dried, spray-dried powder or in the form of a spray, carbohydrate film, functional food, lozenge, tablet (including a soft melt tablet), capsule, and a dose form including a troche or paste. Preferably, the pharmaceutical composition is in a buccal or sublingual dosage form. The buccal or sublingual dosage form could be a paste, capsule or mucoadhesive tablet. A mucoadhesive tablet optionally disintegrates into mucoadhisive particles. The capsule used in a capsule dosage form can be gelatin, pullulan or hypromellose.

A liquid composition according to the invention can be a suspension of liquid crystalline particles or bulk phase in liquid. The liquid is optionally water, physiological saline, simulated body fluids or aqueous buffer. Examples of appropriate buffers include but are not limited to physiologically acceptable buffers, such as, for example, phosphate, phosphate buffered saline (PBS), tris(hydroxymethyl)aminomethane (Tris), 4-(2-hydroxyethyl)-1-piperazineethanesulfonic acid (HEPES), Tris-sucrose, Tris-glycine, and glycine buffers. Most preferably, the hydrophilic solvent is a buffered solution with some isotonicity for the self-assembled structure (to assist with retention of its phase and to be biocompatible) for in vivo use. The liquid composition optionally also comprises other components, including, for example, salts, pH buffering agents and/or sugars such as glucose and sucrose. A liquid composition is optionally administered as a spray or as drops. Both of these forms can be suitable for buccal, sublingual or nasal administration.

A solid or semisolid composition is optionally combined with a hydrophilic solvent prior to administration or administered along with a hydrophilic solvent. Where the composition is combined with a hydrophilic solvent the composition is optionally administered as a spray or drops.

In all embodiments of the composition of the invention, the amphiphilic compound is capable of self-assembling in to liquid crystalline particles upon contact with a hydrophilic solvent. The self-assembled structure formed optionally includes the active ingredient and/or any stabiliser. In liquid forms of the invention the amphiphilic compound is assembled, whereas for solid forms of the invention the amphiphilic compound will only assemble into liquid crystalline particles when there is contact with a hydrophilic solvent.

The present invention has a number of specific forms as set out below. Additional embodiments are of these forms are as discussed elsewhere in the specification. The following aspects of the invention further describe options for the composition of the invention. For example, the present invention provides a composition comprising an amphiphilic compound capable of self-assembling into a liquid crystalline phase, a statin compound and a disintegrant, wherein the composition is formulated for administration via oral mucosa, wherein the w/w ratio of amphiphilic compound to active ingredient is 10:1 to 1:100 and wherein the disintegrant is 10 to 80% w/w of the composition. Preferably, the statin is rosuvastatin. The composition, amphiphilic compound, statin and disintegrant are as described above.

The present invention provides a composition comprising an amphiphilic compound capable of self-assembling into a liquid crystalline phase, a statin compound and a disintegrant, wherein the composition is formulated for administration via oral mucosa, wherein the w/w ratio of amphiphilic compound to active ingredient is 10:1 to 1:100 and wherein the disintegrant is 10 to 80% w/w of the composition, wherein the amphiphilic compound has a critical packing parameter (CPP) of >% and/or a hydrophilic lipophilic balance (HLB) of 0 to >10. Optionally, the CPP is >1 and the HLB is 1 to <8.

In an alternate aspect, the present invention provides a composition comprising an amphiphilic compound capable of self-assembling into a liquid crystalline phase, a statin compound and a disintegrant, wherein the composition is formulated for administration via oral mucosa, wherein the w/w ratio of amphiphilic compound to active ingredient is 10:1 to 1:100, wherein the disintegrant is 10 to 80% w/w of the composition and the statin compound is rosuvastatin, and optionally the amphiphilic compound is glycerol monooleate.

In an alternate aspect, the present invention provides a composition comprising an amphiphilic compound capable of self-assembling into a liquid crystalline phase, rosuvastatin and a disintegrant, wherein the composition is formulated for administration via oral mucosa, wherein the w/w ratio of amphiphilic compound to active ingredient is 10:1 to 1:100, wherein the disintegrant is 10 to 80% w/w of the composition and the composition is stable for at least 6 months. Preferably, the amphiphilic compound is glycerol monooleate, the composition is an ODT and optionally the ODTs is stable at 25° C./60% RH and/or stable at 5° C. for at least 6 months. More preferably, the composition retains 90% or 95% of the active ingredient following storage at either 25° C./60% relative humidity or 5° C. for at least 6 months.

The following aspects of the invention further describe options for the method of lowering blood cholesterol levels in a subject. For example, in one aspect, the present invention provides a method of lowering blood cholesterol levels in a subject in need thereof comprising administering an ODT to the oral mucosa of the subject, wherein the ODT comprises an amphiphilic compound capable of self-assembling into a liquid crystalline phase and a statin compound, and wherein the statin compound is systemically administered via oral mucosa. Preferably, the ODT is for sublingual or buccal administration.

In one aspect, the present invention provides a method of lowering blood cholesterol levels in a subject in need thereof comprising administering an ODT to the oral mucosa of the subject, wherein the ODT comprises an amphiphilic compound capable of self-assembling into a liquid crystalline phase and a statin compound, wherein the statin compound is systemically administered via oral mucosa and the dose of the statin is 0.5 to 30 mg/day, preferably 5 mg/day.

In one aspect, the present invention provides a method of lowering blood cholesterol levels in a subject in need thereof comprising administering an ODT to the oral mucosa of the subject, wherein the ODT comprises an amphiphilic compound capable of self-assembling into a liquid crystalline phase and a statin compound, wherein the statin compound is systemically administered via oral mucosa and the method reduces the total cholesterol in the subject by about 15% to about 30%, preferably about 20% to about 25% or a reduction in the LDL-C in the subject by about 25% to about 50%, preferably about 30% to about 40%. Preferably, the reduction in total cholesterol or LDL-C occurs within 6 weeks of daily administration or the ODT, preferably within 2 weeks.

In one aspect, the present invention provides a method of lowering blood cholesterol levels in a subject in need thereof comprising administering an ODT to the oral mucosa of the subject, wherein the ODT comprises an amphiphilic compound capable of self-assembling into a liquid crystalline phase and a statin compound, wherein the statin compound is systemically administered via oral mucosa and the maximum blood concentration of the active ingredient occurs over 30 minutes following administration of the ODT, preferably 4 hours following administration of the ODT.

In one aspect, the present invention provides a method of lowering blood cholesterol levels in a subject in need thereof comprising administering an ODT to the oral mucosa of the subject, wherein the ODT comprises an amphiphilic compound capable of self-assembling into a liquid crystalline phase and rosuvastatin, preferably micronized rosuvastatin, wherein the rosuvastatin is systemically administered via oral mucosa. Preferably the method administers 5 mg/day rosuvastatin and reduces the total cholesterol in the subject by about 15% to about 30%, more preferably about 20% to about 25%, or a reduction in the LDL-C in the subject by about 25% to about 50%, more preferably about 30% to about 40%. Preferably, the reduction in total cholesterol or LDL-C occurs within 6 weeks of daily administration or the ODT, preferably within 2 weeks.

The following aspects of the invention further describe options for the composition used in the method of lowering blood cholesterol levels in a subject. For example, in one aspect, the present invention provides a method of lowering blood cholesterol levels in a subject in need thereof comprising administering ODT to the oral mucosa of the subject, wherein the ODT comprises an amphiphilic compound capable of self-assembling into a liquid crystalline phase and a statin compound, wherein the statin compound is systemically administered via oral mucosa and the amphiphilic compound is glycerol monooleate and, preferably about 1 to 20% w/w of the ODT.

In one aspect, the present invention provides a method of lowering blood cholesterol levels in a subject in need thereof comprising administering an ODT to the oral mucosa of the subject, wherein the ODT comprises an amphiphilic compound capable of self-assembling into a liquid crystalline phase and rosuvastatin, preferably micronized rosuvastatin, wherein the rosuvastatin is systemically administered via oral mucosa and maximum blood concentration of the rosuvastatin occurs in the subject over 30 minutes following administration of the ODT, preferably 4 hours following administration of the ODT.

In one aspect, the present invention provides a method of lowering blood cholesterol levels in a subject in need thereof comprising administering an ODT to the oral mucosa of the subject, wherein the ODT comprises an amphiphilic compound capable of self-assembling into a liquid crystalline phase and a statin compound, wherein the statin compound is systemically administered via oral mucosa and wherein the composition further comprises a disintegrant, preferably the disintegrant present at an amount of about 1 to about 60% w/w of the ODT. In preferred embodiments, disintegration of the ODT occurs in less than 120 seconds following administration.

In one aspect, the present invention provides a method of treating or preventing statin-intolerance comprising administering a composition according to this invention or following a method of lowering blood cholesterol according to this invention. Preferably, the statin-intolerance is statin-induced myalgia, statin-induced myositis and/or statin-induced myopathy.

In another aspect, the present invention provides a method of transitioning a subject from oral (gastro-intestinal tract delivered) statin treatment to oral mucosal delivered statin treatment comprising (i) ceasing the oral (gastro-intestinal tract delivered) statin treatment and (ii) 1 to 12 days after ceasing the oral (gastro-intestinal tract delivered) statin treatment commencing oral mucosal delivered statin treatment, wherein the oral mucosal delivered statin treatment comprises administering a composition according to this invention or following a method of lowering blood cholesterol according to this invention. Preferably, the oral (gastro-intestinal tract delivered) statin treatment is 5, 10, 20 or 40 mg per day oral rosuvastatin or 10, 20, 40 or 80 mg per day atorvastatin. Preferably, the transition from oral (gastro-intestinal tract delivered) statin to oral mucosal delivered statin further reduces the subject's total cholesterol, maintains the subject's reduction in total cholesterol or minimises the subject's increase in total cholesterol. Optionally, the dose of oral mucosal delivered statin is lower than the dose of oral (gastro-intestinal tract delivered) statin. Optionally, the oral (gastro-intestinal tract delivered) statin is 80 mg per day atorvastatin and the oral mucosal delivered statin is 5 mg rosuvastatin.

In a further aspect, the present invention provides a method for confirming that an ODT according to the invention self assembles into liquid crystalline particles following contact with a hydrophilic solvent comprising dissolving an ODT according to the invention in a hydrophilic solvent to produce a suspension and analysing the suspension using the SAXS/WAXS beamline of a synchrotron to determine if liquid crystalline particles are present. Optionally, the exposure time is 5 seconds. Optionally the suspension is prepared at ambient temperature (eg about 22° C.) and the analysis occurs at ambient temperature (eg about 22° C.).

As used herein, except where the context requires otherwise, the term "comprise" and variations of the term, such as "comprising", "comprises" and "comprised", are not intended to exclude further additives, components, integers or steps.

Further aspects of the present invention and further embodiments of the aspects described in the preceding paragraphs will become apparent from the following description, given by way of example and with reference to the accompanying drawings.

DETAILED DESCRIPTION OF THE EMBODIMENTS

Figure 1:
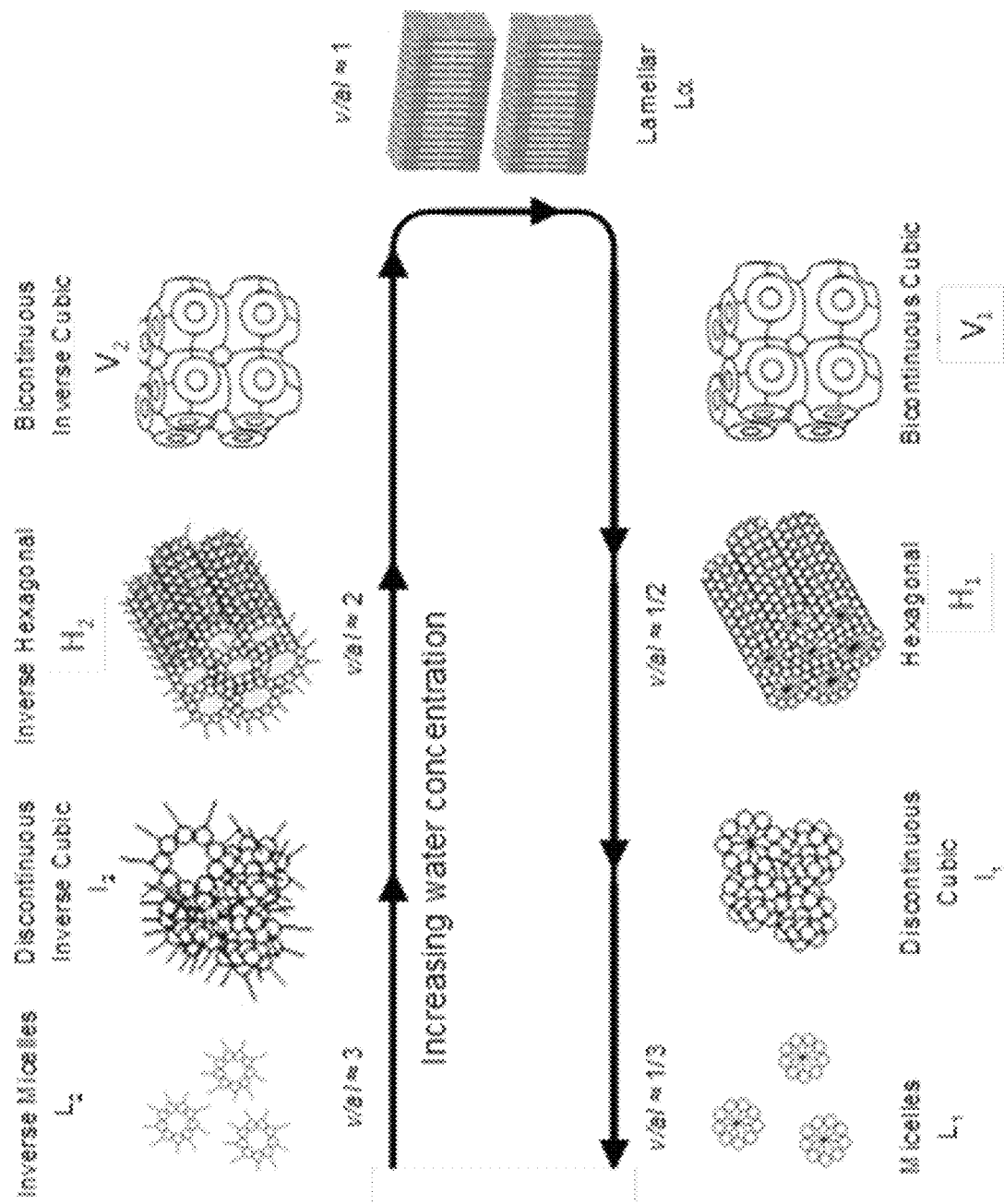
FIG. 1—Outline of the lyotropic liquid crystalline phases that can be formed when water is added to an anhydrous lipid. Normal (o/w) phases are designed I and inversed (w/o) phases II with decreasing packing parameter as water concentration increase. Adapted with permission from Israelachivili et al. (1994) and Nguyen (2009). Israelachvili, J., The science and applications of emulsions—an overview. Colloids Surf. Physico chem. Eng. Aspects 1994, 91, 1-8. Nguyen, T.-H. Investigation of novel liquid crystalline materials for the sustained oral delivery of poorly water soluble drugs. PhD, Monash University, Melbourne, 2009.

It will be understood that the invention disclosed and defined in this specification extends to all alternative combinations of two or more of the individual features mentioned or evident from the text or drawings. All of these different combinations constitute various alternative aspects of the invention.

Reference will now be made in detail to certain embodiments of the invention. While the invention will be described in conjunction with the embodiments, it will be understood that the intention is not to limit the invention to those embodiments. On the contrary, the invention is intended to cover all alternatives, modifications, and equivalents, which may be included within the scope of the present invention as defined by the claims.

Further aspects of the present invention and further embodiments of the aspects described in the preceding paragraphs will become apparent from the following description, given by way of example.

All of the patents and publications referred to herein are incorporated by reference in their entirety.

For purposes of interpreting this specification, terms used in the singular will also include the plural and vice versa.

One skilled in the art will recognize many methods and materials similar or equivalent to those described herein, which could be used in the practice of the present invention. The present invention is in no way limited to the methods and materials described.

The inventors of the present invention have developed compositions for administration of one or more statins and methods or delivering statins which avoid the gastrointestinal side effects of oral dosage forms including statins and the problems of first past metabolism allowing a lower dose of statin to be administered to achieve efficacy. The compositions are for administration via oral mucosa such as via buccal or sublingual delivery. Delivery of an active ingredient via oral mucosa can be too rapid, therefore, the present invention combines the statin and an amphiphilic compound capable of assembly into a liquid crystal particle upon contact with a hydrophilic solvent. The presence of the amphiphile appears to slow down or prolong absorption of the statin (when compared to a traditional ODT).

Surprisingly, administration of the rosuvastatin containing composition of the invention via oral mucosa to patients was not only effective but achieved reductions in blood cholesterol faster than those published for oral Crestor (see the Crestor Product Information as amended on 18 Aug. 2015, a copy of which is incorporated by reference in its entirety. The clinical trials of particular interest are at pages 3 to 8).

The term 'self-assembled particles' as used throughout the specification is understood to mean an aggregate of amphiphiles that possess some degree of internal organisational order, for example, a colloidal particle or colloidosome or a solid lipid particle. The particles can be either nanoparticles or microparticles depending on their average size, typically less than about 1 μm, preferably in a range of about 10 nm to about 500 nm, more commonly about 200 nm. Solid lipid nanoparticles are a dispersed crystalline lamellar lipidic material. The self-assembled particles are formed by contacting the amphiphile with solvent. In some embodiments, the self-assembled particles themselves aggregate into a bulk lyotropic phase.

The term 'bulk phase' as used throughout the specification is understood to mean a lyotropic phase that includes but is not limited to: micellar cubic (I1); normal hexagonal (H1); bicontinuous cubic (V1); lamellar (L); reversed bicontinuous cubic (V2); reversed hexagonal (H2); reversed micellar cubic (I2) and sponge (L3) phases.

The term 'cubic phase' as used throughout the specification is understood to refer to two main classes of phases: micellar cubic and bicontinuous cubic. 'Micellar cubic phase' refers to a phase consisting of spherical micelles arranged in a cubic array. A 'normal micellar cubic phase' or 'II phase' consists of spherical normal micelles arranged in a cubic array, whilst an 'inverse micellar cubic phase' or 'III phase' consists of spherical inverse micelles arranged in a cubic array. 'Bicontinuous cubic phase' refers to a family of closely related phases that consist of a single curved lipid bilayer that forms a complex network that separates the polar solvent space into two continuous, but non-intersecting volumes. Bicontinuous cubic phases possess long range order based upon a cubic unit cell. Bicontinuous cubic phases have zero mean curvature; that is, at all points on surface of the amphiphile bilayer, the surface is as convex as it is concave. Bicontinuous cubic phases include the normal ('vi phase') or reverse ('vII phase') type. Several types of long range orientational orders have been observed for bicontinuous cubic phases; the orientational order in these phases correspond to space groups Ia3d, Pn3m, and Im3m. When a colloidosome possesses the internal structure of a bulk cubic phase the colloidosome is referred to as a 'cubosome'.

The term 'hexagonal phase' as used throughout the specification is to be understood to mean an amphiphile phase consisting of long, rod-like micelles packed into a hexagonal array. A 'normal hexagonal phase' is a hexagonal phase consisting of long, rod-like normal micelles, whilst an 'inverse hexagonal phase' is a hexagonal phase consisting of long, rod-like inverse micelles. The normal hexagonal phase is also referred to as the 'HI phase' and the inverse hexagonal phase is also referred to as the 'HII phase'. When a colloidosome possesses the internal structure of a bulk hexagonal phase the colloidosome is referred to as a 'hexosome'.

The term 'lamellar phase' as used throughout the specification is to be understood to mean a stacked bilayer arrangement, where opposing monolayers of the hydrophilic portion of amphiphile molecules are separated by a polar solvent domain, while the hydrophobic portion of the amphiphile molecule of the back-to-back layers are in intimate contact to form a hydrophobic layer. The planar lamellar phase is referred to as the 'Lα phase'. There are three lamellar phases, (1) the fluid lamellar phase (Lα) where the chains are melted, (2) the gel lamellar phase (Lß) where the chains are mostly melted but some degree of short range order and (3) the lamellar crystalline phase (Lc), where the chains are crystalline with very short range order.

The term 'sponge phase' or 'L3 phase' as used throughout the specification refers to a phase that resembles a bicontinuous cubic phase, in that it possesses an amphiphile bilayer that separates the polar solvent space into two unconnected volumes, but it does not possess long range order. Accordingly, these phases are analogous to a 'melted cubic phase'.

The term 'prodrug' as used throughout the specification refers to a biologically active agent including structural modifications thereto, such that in vivo the prodrug is converted, for example, by hydrolytic, oxidative, reductive or enzymatic cleavage to the biologically active agent by one or more reactions or steps. It includes an agent that requires one or more chemical conversion steps or steps of metabolism to produce the active molecule.

The term 'pharmaceutical composition' as used throughout the specification means a composition comprising a therapeutically effective amount of at least one statin according to the current invention. The pharmaceutical composition optionally further include one or more of a pharmaceutically acceptable carrier, excipient, diluent, additive or vehicle selected based upon the intended form of administration, and consistent with conventional pharmaceutical practices. Suitable pharmaceutical carriers, excipients, diluents, additives and vehicles are known to those skilled in the art.

As used herein, 'therapeutically effective amount' relates to the amount or dose of a statin or other active thereof that will lead to one or more desired effects, in particular the reduction of cholesterol synthesis. A therapeutically effective amount of a statin will vary according to factors such as the disease state, age, sex, and weight of a subject, and the ability of the substance to elicit a desired response in the subject.

Structure of Oral Mucosa

In general terms, the oral mucosa is made up of an outermost layer of stratified squamous epithelium, which is covered with the mucous and consists of stratum distendum, stratum filamentosum, stratum suprabasale, and a stratum basale. Below these lie a basal lamina, the lamina propria, and the sub mucosa. The epithelium serves as the mechanical barrier that protects underlying tissues, whereas the lamina propria acts as a mechanical support and also carries the blood vessels and nerves. Some regions of the oral mucosa are keratinized, whereas others are not. The non-keratinized regions, such as buccal and sublingual are more permeable than the keratinized regions. This is due to some extent to composition of intracellular lipids comprising neutral lipids (Ceramides). Non-keratinized areas are composed of glycosyl ceramides that appear to differ morphologically from the lamellate membrane coating granules of keratinized tissue.

Because the oral mucosa is highly vascularized, drugs that are absorbed through the oral mucosa directly enter the systemic circulation, bypassing the gastrointestinal tract and first-pass metabolism in the liver. For some drugs, this results in rapid onset of action via a more comfortable and convenient delivery than the intravenous route. Not all drugs, however, can be administered through the oral mucosa because of its characteristics and physicochemical properties of the drug. For example, the active pharmaceutical ingredient may be lipophilic and therefore be repelled by the aqueous mucous layer under the tongue. Newer carriers such as cubosomes can overcome these barriers by having both water loving and lipid loving components, facilitating miscibility with the mucous membrane. This property can be described as amphiphillic or possessing both water and fat solubility.

The mucosal lining of the oral cavity is readily accessible, robust, and heals rapidly after local stress or irritation. Sublingual drug delivery systems can be localized easily and are well accepted by patients. The oral cavity can therefore serve as a site for more efficient systemic drug delivery. The total surface area of the oral cavity is about 100 cm. The mucosal membranes of the oral cavity can be divided into five regions: the floor of the mouth (sublingual), the buccal mucosa (cheeks), the gums (gingiva), the palatal mucosa, and the lining of the lips. These oral mucosal regions are different from each other in terms of anatomy, permeability to drug, and their ability to retain a system for a desired length of time. The buccal mucosa is less permeable than the sublingual mucosa. Due to similarities of the oral and nasal mucosa including structure and function, the liquid crystalline delivery system taught is useful for both delivery routes.

Liquid Crystalline Particles

There are multiple forms of liquid crystalline particles each with different structure. The self-assembled structure may be micellar (normal or reversed), lamellar, hexagonal (normal or reversed), cubic (normal discrete, reversed discrete, reversed bicontinuous—including primitive, gyroid and diamond—or reversed discontinuous), or other 'intermediate phases' such as the ribbon, mesh, or non-cubic 'sponge' bicontinuous phases. When these particles possess the internal structure of a reversed bicontinuous cubic phase, the particles are colloquially referred to as cubosomes. Similarly, when the particles possess the internal structure of a reversed hexagonal phase, they are referred to as hexosomes. When the particles possess the internal structure of a lamellar phase, they are referred to as liposomes.

The type of phase structures formed is dependent on the amphiphile structure, amphiphile concentration, temperature, pressure and solvent content (Kaasgaard, T.; Drummond, C. J., Ordered 2-D and 3-D nanostructured amphiphile self-assembly materials stable in excess solvent. *Phys. Chem. Chem. Phys.* 2006, 8, 4957-4975). The relationship between phase structures formation and the geometry of amphiphilic molecules can be defined by the dimensionless critical packing parameter $(p)=v/al$ where v and l are the volume and the length of the fully extended hydrocarbon chain and a is the surface area of the hydrophilic headgroup. An increase in a can occur due to an increase in hydration and electrostatic repulsion between adjacent hydrophilic headgroups. Whilst an increase in v can be due to increases in hydrocarbon chain fluidity at elevated temperature or increases in the number, branching and/or size of the hydrocarbon chain. At p=1, which indicates equal hydrophilic and hydrophobic volume, lamellar (Lα) bilayer structure are formed. Normal (Type 1) self-assembled structure with the interface curves spontaneously towards water (positive curvature) are formed when p<1 whilst inverse structures (Type 2) with interface curves spontaneously away from water (negative curvature) are formed when p>1. In addition to micellar (p<1/3), inverse micellar (p>3) and lamellar structures, other phases such as the two dimensional normal and inverse hexagonal (H1 and H2), the three dimensional normal and inverse bicontinuous cubic (V1 and V2) and the discontinuous cubic (I1 and I2) phases are also observed (structure to be discussed in detail later). It should be noted that a range of nomenclatures are used in literature to denote the individual phase in the literature, so for this report, the abbreviations just mentioned will be utilised.

Lamellar, hexagonal and cubic phases are considered as liquid crystal phases as they exhibit both the long range order of crystalline materials and the disorder of liquid systems.

For conventional surfactants, a progressive increase in the water content induces changes in the phase structure from inverse phases to normal phases as illustrated in FIG. 1.1. Not all structures illustrated in FIG. 1.1 may be observed, but the order and progression of the general phase change is preserved.

However, some amphiphilic molecules do not follow the illustrated lyotropic phase behaviour in FIG. 1.1 all the way to micelles in addition water. These molecules only swell in contact with water to a finite degree and forms liquid crystalline phases depending on their chemical structure, and further addition of water does not induce the transition to micelles. Hence these inverse LC phases co-exist with excess water at very high dilution. The most well-known example of this behaviour is phospholipids which remain as Lα phase in excess water and are the critical component of cellular membranes.

Lamellar Liquid Crystals

Lamellar liquid crystal (LC) phases consist of stacked bilayers, where lipid molecules are arranged so that the hydrophobic chains meet to form a hydrophobic domain whilst the hydrophilic head groups facing opposite ends form the hydrophilic domains with other lamellae bilayers. Water occupies the hydrophilic domain and interacts with the hydrophilic head groups lining each lamellae. The lamellar liquid crystals are formed when the geometric space occupied by the hydrophilic headgroup and the hydrophobic tail are equivalent (packing parameter 1). Lamellar structures are the arguably the most ubiquitous liquid crystal structure of all lyotropic liquid crystals as they are featured in most biological membranes.

Cubic Liquid Crystals

Micellar Cubic Structures (I)

Discontinuous cubic phases (as opposed to the bicontinuous cubic phases discussed later) are micelles embedded in a three-dimensional, matrix organised in a cubic symmetry. The discontinuous cubic phases, whether normal (I1) or inverted (I2) are intermediate LC phases and reside between hexagonal LCs and micelles in the order of progression described in FIG. 1.

Bicontinuous Cubic Liquid Crystals (V)

Bicontinuous cubic LC phases, whether normal V1 or inverse V2 are viscous, optically isotropic liquid crystals located on either side of the lamellar structure and differ from the discontinuous cubic phases, as they consists of separate but continuous lipid bilayer and water regions.

The inverse bicontinuous cubic phase (V2) consists of two separate, continuous but nonintersecting hydrophilic regions divided by a single lipid bilayer in a complex 3-D cubic symmetry. It is generally believed that V2 phases have interface structures based on the infinite periodic minimal surfaces (IPMS), where the lipid surface consists of two principle curvatures which are equal but opposite in sign at every point (as convex as they are concave), resulting in zero average mean curvature (positive+negative curvature), and negative Gaussian curvature (positivex negative curvature). Using X-ray scattering measurements the existence of cubic phases in amphiphile+water systems was recognized in the 60s. Although mathematicians have found a wide variety of periodic minimal surfaces, only three types of IPMS have been observed in amphiphile-water systems: Gyriod (G), double diamond (D) and primitive (P) with corresponding space groups of Ia3d (G), Pn3m (D) and Im3m (P), respectively (see FIG. 1). The different phases can be identified by their unique X-ray scattering patterns.

Hexagonal Liquid Crystals (H)

Hexagonal LCs are designated as either H1 (normal) or inverse H2 phases. The H phases are viscous, optically birefringent liquid crystals consisting of infinitely long hexagonally close packed cylindrical micelles (see FIG. 1). The H2 phase has more negative curvature than the inverse cubic phase due to larger hydrophobic portion of the molecules.

Bulk Phase

The liquid crystalline particles of the present invention optionally self-assembled into bulk phase including an active ingredient. Typically, a bulk material having a certain phase will form from an amphiphile, that is, a molecule that possesses both a hydrophilic portion and a hydrophobic portion. The self-assembly behaviour of amphiphiles in solvent arises because of the preferential interaction between the solvent and either the hydrophilic or hydrophobic portion of the amphiphilic molecule. When an amphiphile is exposed to a polar solvent, the hydrophilic portion of the amphiphile tends to preferentially interact with the polar solvent, resulting in the formation of hydrophilic domains. The hydrophobic portion of the amphiphile molecules tend to be excluded from this domain, resulting in the de facto formation of a hydrophobic domain.

It is in a self-assembled form that amphiphiles are capable of acting as an inert carrier or matrix into which biologically active molecules, such as an active ingredient, may be incorporated. The nanoscale porosity of the self-assembled materials provides a high internal and external surface area. An active ingredient that is distributed within a region of this material is believed to be distributed in an ordered arrangement, and at a high loading concentration due to the large internal and external liquid crystal surface area. Self-assembled bulk phase may exhibit a variety of orientational orders. If long-range orientational order is observed within the self-assembled bulk phase at equilibrium, the self-assembled bulk phase is termed a 'mesophase', a 'lyotropic liquid crystalline phase', a 'lyotropic phase' or, as used herein, simply a 'phase'.

There are 2 principal types of liquid crystalline phases: thermotropic liquid crystals and lyotropic liquid crystals. Thermotropic liquid crystals can be formed by heating a crystalline solid or by cooling an isotropic melt of an appropriate solute. Lyotropic liquid crystals can be formed by addition of a solvent to an appropriate solid or liquid amphiphile. The manipulation of parameters such as amphiphile concentration and chemical structure, solvent composition, temperature and pressure may result in the amphiphile-solvent mixture adopting lyotropic phases with distinctive characteristics.

Examples of particular phases that can be formed by self-assembled particles are set out above. It is possible to disperse the bulk phases described above to form colloidal particles (so-called 'colloidosomes') that retain the internal structure of the non-dispersed bulk phase. When these particles possess the internal structure of a reversed bicontinuous cubic phase, the particles are colloquially referred to as cubosomes. Similarly, when the particles possess the internal structure of a reversed hexagonal phase, they are referred to as hexosomes. When the particles possess the internal structure of a lamellar phase, they are referred to as liposomes.

Whilst the bulk materials can be of use in some circumstances, the use of bulk materials having cubic phases in drug administration is limited by their high viscosity making them difficult to administer. In these cases, colloidal dispersions of particles of these cubic phases can be used in drug delivery. More preferred phases for use as drug delivery vehicles are bicontinuous cubic phase or reversed hexagonal phase. The inverse cubic phase affords distinct aqueous regions that form two continuous water networks (or channels) throughout the cubic phase that more readily allow diffusion of an active ingredient. The inverse cubic liquid crystal phase is thermodynamically stable and co-exists in equilibrium with excess water over a broad temperature range. Alternatively, if the bicontinuous cubic phase is viscous and difficult to administer it may be possible to administer a lamellar phase material that converts into the cubic phase upon dissolution with aqueous, water rich, body fluids (thus facilitating the conversion of one phase to another). For example, a suitable material is a phospholipid such as 1,2-dioleoyl-sn-glycero-3-phosphocholine. The cubic phase in situ provides a viscous depot from which an active ingredient can slowly be released. An inverse cubic liquid crystal phase provides an appropriate scaffold in which to distribute or load the niacin compound owing to the high surface area of the internal liquid crystal structure (up to 400 m2/g).

One of the key difficulties with using liquid crystalline particles in the formulation of dosage forms for active ingredient delivery has been the viscosity of many liquid crystalline phases, which are difficult to handle, difficult to manufacture and difficult to administer.

The composition optionally includes 1 to 40 mg statin. Alternatively, 1 to 15 mg statin or 1 to 10 mg statin. Preferred compositions include about 5 mg statin, for example, 5 mg rosuvastatin.

Suitable pharmaceutical carriers, excipients, diluents, additives and vehicles are known to those skilled in the art.

The formulation optionally includes one or more binders such as hydroxypropylmethylcellulose (HPMC), ethyl cellulose, acacia, polyvinyl alcohol (PVA), and polyvinylpyrrolidone (Povidone).

The formulation optionally includes one or more glidants such as talc, magnesium trisilicate and colloidal silicon dioxide.

The formulation optionally includes one or more fillers such as lactose, mannitol, sorbitol, starch, maltodextrin, acacia and silicon dioxide.

The formulation optionally includes one or more lubricants such as glyceryl behenate, stearic acid, talc, zinc stearate, calcium stearate, magnesium stearate, aluminium stearate and sodium stearyl fumarate.

The formulation optionally includes one or more film formers such as hydroxypropylmethylcellulose (HPMC), povidone (PVP), poly ethylene glycol (PEG).

The formulation optionally includes one or more pH modifier agents (buffering agents) such as sodium hydroxide, sodium/calcium carbonate, citric acid, tartaric acid, fumaric acid etc.

If the formulation is prepared by thermoplastic granulation the formulation optionally includes thermoplastic granulation agents such as glycerol monostearate, and glyceryl behenate.

Other excipients may be added to the composition such as: surfactants (anionic/cationic/nonionic), pH dependent/independent polymers, pH modifier agents (buffering agents), sweeteners/flavoring agents, chelating agents, stabilizers, mucoadhesive agents, coloring agents etc.

The presence of liquid crystalline phase can be determined using the SAX/WAX beamline of a synchrotron, cross polarised light microscopy (CPLM) or Cry-Em. In certain circumstances, such as a low proportion of amphiphilic compound in the ODT, liquid crystalline phase may not be identified using the SAX/WAX beamline of the synchrotron and an alternative, such as, CPLM may be preferred. CPLM can identify LC structures but does not provide information on the internal phase.

The CPP of an amphiphilic compound can be determined by quantum mechanics molecular simulations to determine geometrical and quantitative structure-activity relationship (QSAR) values. See, Fong 2016. The HLB of an amphiphilic compound is calculated based on the number and identity of hydrophilic/lipophilic groups.

The CPP and HLB of some amphiphilic compounds are in Table A.

TABLE A

CPP and HLB for various amphiphilic compounds

| Amphiphile | CPP | V | $A_0$ | $L_C$ | HLB |
|---|---|---|---|---|---|
| Phytantriol | 0.650 | 303.5 | 27.9 | 16.8 | 6.36 |
| Monolinolein | 1.016 | 341.0 | 22.6 | 14.8 | 1.02 |
| Glucose stearate | 0.456 | 315.3 | 31.2 | 22.2 | 9.28 |
| Fructose stearate | 0.421 | 315.3 | 33.8 | 22.2 | 9.28 |

The active ingredients melatonin and atenolol have been shown to load and release from a monoolein-water liquid crystalline system previously and are expected to be compatible with the ODT of this invention. Atropine, haloperidol, levofloxacin, indomethacin, diazepam, trans retinol, prednisolone, progesterone, hydrocortisone and dexamethasone have been shown to load an release from monoolein and/or phytantriol liquid crystals previously and are expected to be compatible with the ODT of this invention. Irinotecan and paclitaxel has also been released from inverse hexagonal phase previously and are expected to be compatible with the ODT of this invention.

REFERENCES

The text of each of the following references is incorporated by reference into this specification.

Caffrey, M.; Cheng, A., Kinetics of lipid phase changes. *Curr. Opin. Struct. Biol.* 1995, 5, 548-555.

Chang, C.-M.; Bodmeier, R., Low viscosity monoglyceride-based drug delivery systems transforming into a highly viscous cubic phase. *Int. J. Pharm.* 1998, 173, 51-60.

Clogston, J.; Rathman, J.; Tomasko, D.; Walker, H.; Caffrey, M., Phase behavior of a monoacylglycerol (Myverol 18-99K)/water system. *Chem. Phys. Lipids* 2000, 107, 191-220.

Drummond, C. J.; Fong, C., Surfactant self-assembly objects as novel drug delivery vehicles. *Current Opinion in Colloid & Interface Science* 1999, 4, 449-456.

Fong, W et al, Dynamic formation of nanostructured particles from vesicles via invertase hydrolysis for on-demand delivery, *The Royal Society of Chemistry: Electronic Supplementary Material (ESI) for RSC Advances*, 2016, S1-S22.

Hyde, S. T., Bicontinuous structures in lyotropic liquid crystals and crystalline hyperbolic surfaces. *Current Opinion in Solid State and Materials Science* 1996, 1, 653-662.

Israelachvili, J., The science and applications of emulsions—an overview. Colloids Surf. Physico chem. Eng. Aspects 1994, 91, 1-8.

Kaasgaard, T.; Drummond, C. J., Ordered 2-D and 3-D nanostructured amphiphile self-assembly materials stable in excess solvent. *Phys. Chem. Chem. Phys.* 2006, 8, 4957-4975)

Martin, P. et al, Pharmacodynamic effects and parhmacokinetics of a new HMG-CoA reductase inhibitor, rosuvastatin, after morning or evening administration in healthy volunteers, *Br J Clin Pharmacol*, 2002, 54, 472-477.

Zhang, D. et al, Validated LC-MS/MS method for the determination of rosuvastatin in human plasma: application to a bioequivalence study in Chinese volunteers, *Pharmacology & Pharmacy*, 2011, 2, 341-346.

Example 1—Spray Dried Formulation

TABLE 1

Spray dried formulation

| Ingredient | Range (%) | Notes |
|---|---|---|
| Suspension for Spray Drying | | |
| Mannitol | 30-90 | Carrier, Filler |
| Povidone (Poly vinyl pyrrolidone) - Optional | 0-20 | Binder, film former |
| Rosuvastatin Calcium (micronized) | 1-15 * | Drug substance/API |
| Glyceryl Monooleate (GMO) | 1-20 | Bioadhesive/Mucoadhesive agent, Gelling agent, nonionic surfactant, sustained release agent |
| Purified Water | N/A | Solvent |
| Ethanol | N/A | Solvent |
| Dry Mix - Final blend for compression | | |
| Pharmaburst (mixture of Mannitol, Sorbitol Crosspovidone & Silicon dioxide) | 0-50 | Filler, Taste masking, Disintegration agent. |
| Sodium Starch Glycolate | 0.5-20 | Disintegration agent |
| Colloidal Silicon Dioxide | 0.5-3.0 | Glidant |
| Magnesium Stearate | 0.5-2.0 | Lubricant |

* The above formulation example may contain 1-40 mg of Rosuvastatin.

Manufacturing Process

For the preparation of the spray dried powder, mannitol was dissolved in water until a clear solution was obtained; the Rosuvastatin was dispersed in melted GMO and Ethanol. The Rosuva:GMO dispersion was then added to the formed Mannitol solution to form uniform suspension which was then spray dried. The obtained spray dried granules were then blended with the extra-granule excipients to form the final blend for compression.

Synchrotron Testing

The spray dried granules (cubosome precursors) were tested at the Australian Synchrotron to verify cubic structure formation upon hydration. The results show clear cubic structure formation in PBS & Saliva.

Spray drying does not impact on formation of the liquid crystal structures:

TABLE 2

Liquid crystalline structure for SBT089

| Spray dried powder blend (GMO:rosuvastatin) | Structure obtained in PBS | Structure obtained in Saliva |
|---|---|---|
| SBT089 (2.5:1) | Pn3m | Im3m |

Example 2—Thermoplastic Granulation Formulation

TABLE 3

Thermoplastic granulation formulation

| Ingredient | Range (%) | Notes |
|---|---|---|
| Thermoplastic Granulation | | |
| Mannitol | 30-90 | Carrier |
| Sodium Starch Glycolate - Optional | 0-20 | Disintegration agent |
| Rosuvastatin Calcium | 1-15 * | Drug substance/API |
| Glyceryl Monooleate (GMO) | 1-20 | Bioadhesive/Mucoadhesive agent, Gelling agent, nonionic surfactant, sustained release agent |
| Polyethylene Glycol (PEG) | 1-20 | Thermoplastic agent |
| Povidone (Poly vinyl pyrrolidone) - Optional | 0-20 | Binder |
| Dry Mix - Final blend for compression | | |
| Pharmaburst- Optional (mixture of Mannitol, Sorbitol Crosspovidone & Silicon dioxide) | 0-50 | Filler, Taste masking, Disintegration agent. |
| Sodium Starch Glycolate | 0.5-20 | Disintegration agent |
| Colloidal Silicon Dioxide | 0.5-3.0 | Glidant |
| Magnesium Stearate | 0.5-2.0 | Lubricant |

* The above formulation example may contain 1-40 mg of Rosuvastatin.

Manufacturing Process

For the preparation of the thermoplastic granules, mannitol and sodium starch Glycolate were mixed in high shear mixer (HSM); the Rosuvastatin was dispersed in melted GMO; The Rosuva:GMO dispersion was then added to the HSM while mixing; The Polyethylene Glycol (PEG) was melted and then added into the HSM while mixing to form the thermoplastic granules. The granules were then blended with the extra-granules excipients to form the final blend for compression.

Synchrotron Testing

The compressed tablets were tested at the Australian Synchrotron to verify cubic structure formation upon hydration. The results show clear cubic structure formation in PBS M Saliva.

Example 3—Wet Granulation Formulation

TABLE 4

Wet granulation formulation

| Ingredient | Range (%) | Notes |
|---|---|---|
| Wet Granulation | | |
| Mannitol | 30-90 | Carrier |
| Sodium Starch Glycolate - Optional | 0-20 | Disintegration agent |
| Rosuvastatin Calcium | 1-15 * | Drug substance/API |
| Povidone (Poly vinyl pyrrolidone) - Optional | 0.5-5 | Binder |
| Glyceryl Monooleate (GMO) | 1-20 | Bioadhesive/Mucoadhesive agent, Gelling agent, nonionic surfactant, sustained release agent |
| Ethanol | N/A | Solvent |
| Dry Mix - Final blend for compression | | |
| Pharmaburst - Optional(mixture of Mannitol, Sorbitol Crosspovidone & Silicon dioxide) | 0-50 | Filler, Taste masking, Disintegration agent. |
| Sodium Starch Glycolate | 0.5-20 | Disintegration agent |
| Colloidal Silicon Dioxide | 0.5-3.0 | Glidant |
| Magnesium Stearate | 0.5-2.0 | Lubricant |

* The above formulation example may contain 1-40 mg of Rosuvastatin.

Manufacturing Process

For the preparation of the granules, mannitol and sodium starch Glycolate (optional) were mixed in high shear mixer (HSM); the Rosuvastatin and the Sodium Starch Glycolate (optional) were dispersed in melted GMO; The Rosuva:SLS:GMO dispersion was then added to the HSM while mixing; The Povidone (Poly vinyl pyrrolidone) wasdissolvedinethanol; ThePovidonesolutionwasthenaddedintothe HSM while mixing to form the granules. The obtained granules were then dried and milled. The milled granules were then blended with the extra-granules excipients to form the final blend for compression.

Synchrotron Testing

The compressed tablets were tested at the Australian Synchrotron to verify cubic structure formation upon hydration. The results show clear cubic structure formation in PBS & Saliva.

Example 4—Rosuvastatin Disintegrating Tablets

TABLE 5

5 mg statin formulation with 1:1 GMO to statin (SBT122)

| Ingredient | % w/w | Function |
|---|---|---|
| Mannitol | 75.3 | Filler/Carrier |
| Rosuvastatin Calcium (micronized) | 7.3 | Drug substance/API |
| Povidone (Poly vinyl pyrrolidone) | 1.7 | Binder |
| Glyceryl Monooleate (GMO) | 7.3 | Bioadhesive/Mucoadhesive agent, Gelling agent, nonionic surfactant, sustained release agent |
| Sodium Starch Glycolate | 5.0 | Disintegration agent |
| Colloidal Silicon Dioxide | 2.0 | Glidant |
| Magnesium Stearate | 1.5 | Lubricant |
| Ethanol | N/A * | Solvent |

* Evaporated during the drying process.

TABLE 6

5 mg statin formulation with 7:1 GMO to statin (SBT123)

| Ingredient | % w/w | Function |
|---|---|---|
| Mannitol | 76.0 | Filler/Carrier |
| Rosuvastatin Calcium (micronized) | 1.6 | Drug substance/API |
| Povidone (Poly vinyl pyrrolidone) | 3.4 | Binder |
| Glyceryl Monooleate (GMO) | 10.5 | Bioadhesive/Mucoadhesive agent, Gelling agent, nonionic surfactant, sustained release agent |
| Sodium Starch Glycolate | 5.0 | Disintegration agent |
| Colloidal Silicon Dioxide | 2.0 | Glidant |
| Magnesium Stearate | 1.5 | Lubricant |
| Ethanol | N/A * | Solvent |

* Evaporated during the drying process.

Process for wet granulation manufacturing of both formulations:
  Rosuvastatin calcium was dispersed in melted GMO
  Povidone was dissolved in ethanol
  Mannitol was granulated with the Rosuvastatin:GMO suspension and the Povidone solution
  The granules were dried and milled.
  The milled granules were blended with the remaining excipients to form the final blend for compression.

Disintegration testing was conducted in a basket-rack assembly and in accordance with Appendix XII A. Disintegration of the European Pharmacopoiea edition 9.0 (Ph. Eur. Method 2.9.1). The solvent was water at 37° C.

The formulation of Table disintegrated within 8-10 minutes of contact with oral mucosa and achieved 100% dissolution in media within 15 minutes (Dissolution apparatus II, paddles, 50 rpm, 900 ml, Citrate buffer pH 6.6).

The formulation of Table 6 disintegrated within 45 minutes of contact with oral mucosa and achieved 100% dissolution in media within 120 minutes (Dissolution apparatus II, paddles, 50 rpm, 900 ml, Citrate buffer pH 6.6).

TABLE 7

5 mg statin ODT with 1:1 GMO to statin (SBT 176)

| Ingredient | % w/w | Function |
|---|---|---|
| Pharmaburst - (co-processed mixture of Mannitol, Sorbitol Crospovidone & Silicon dioxide) | 68.67 | Filler, Taste masking, Disintegration agent. |
| Crospovidone XL | 15.00 | Disintegration agent |
| Sodium Chloride | 0.25 | Osmotic agent |
| Sodium Cyclamate | 0.60 | Sweetener |
| Saccharin Sodium | 0.40 | Sweetener |
| Menthol (Optional) | 0.20 | Flavouring agent |
| Rosuvastatin Calcium (micronized) | 5.44 | Drug substance/API |

TABLE 7-continued

5 mg statin ODT with 1:1 GMO to statin (SBT 176)

| Ingredient | % w/w | Function |
|---|---|---|
| Povidone (Poly vinyl pyrrolidone) | 1.50 | Binder |
| Glyceryl Monooleate (GMO) | 5.44 | Bio adhesive/ Mucoadhesive agent, Gelling agent, nonionic surfactant, sustained release agent |
| Sodium Starch Glycolate | 5.00 | Disintegration agent |
| Colloidal Silicon Dioxide | 1.50 | Glidant |
| Magnesium Stearate | 1.00 | Lubricant |
| Ethanol | N/A * | Solvent |

* Evaporated during the drying process.

8 mm round tablets of this formulation were stability tested at 5° C. for 9 months Assay of the 5 mg rosuvastatin showed 97.1% at t=0, 98.1% at t=3 months, 95.8% at t=6 months and 96% at t=9 months. The formulation was also stability tested at 25° C./60% RH for 9 months. Assay of the 5 mg rosuvastatin showed 97.1% at t=0, 94.2% at t=3 months, 96.1% at t=6 months and 94.4% at t=9 months. In addition, the assay of the tablets showed 0.03% at t=0, 0.16% at t=3 months, 0.20% at t=6 months and 0.34% at t=9 months of rosuvastatin in the lactone form and 0.15% at t=0, 0.25% at t=3 months, 0.29% at t=6 months and 0.34% at t=9 months of 5-oxo-rosuvastatin calcium (TP-13 impurity 1) at following storage at 25° C./60% RH. The assay of the tablets also showed 0.03% at t=0, 0.03% at t=3 months, 0.03% at t=6 months and 0.06% at t=9 months of rosuvastatin in the lactone form and 0.15% at t=0, 0.18% at t=3 months, 0.17% at t=6 months and 0.21% at t=9 months of the 5-oxo-rosuvastatin calcium at both 3 and 6 months at 5° C.

The structure of 5-oxo-rosuvastatin calcium is below.

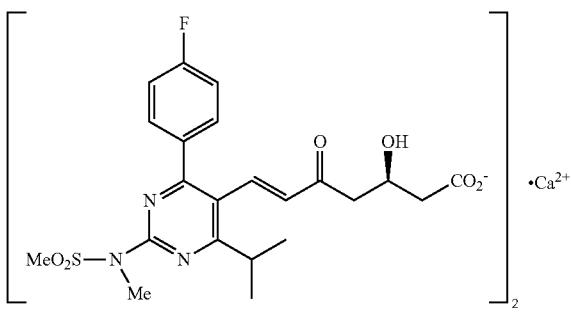

A placebo ODT (SBT183) was also prepared with the formulation of SBT 176 except there is no active ingredient (rosuvastatin).

TABLE 8

5 mg statin ODT with 4:1 GMO to statin (SBT 177)

| Ingredient | % w/w | Function |
|---|---|---|
| Pharmaburst - (co-processed mixture of Mannitol, Sorbitol Crospovidone & Silicon dioxide) | 64.47 | Filler, Taste masking, Disintegration agent. |
| Crospovidone XL | 15.00 | Disintegration agent |
| Sodium Chloride | 0.25 | Osmotic agent |
| Sodium Cyclamate | 0.60 | Sweetener |
| Saccharin Sodium | 0.40 | Sweetener |
| Menthol | 0.20 | Flavouring agent |
| Rosuvastatin Calcium (micronized) | 1.81 | Drug substance/API |
| Povidone (Poly vinyl pyrrolidone) | 2.50 | Binder |
| Glyceryl Monooleate (GMO) | 7.26 | Bio adhesive/ Mucoadhesive agent, Gelling agent, nonionic surfactant, sustained release agent |
| Sodium Starch Glycolate | 5.00 | Disintegration agent |
| Colloidal Silicon Dioxide | 1.50 | Glidant |
| Magnesium Stearate | 1.00 | Lubricant |
| Ethanol | N/A * | Solvent |

* Evaporated during the drying process.

Process for wet granulation manufacturing:
Rosuvastatin calcium was dispersed in melted GMO
Povidone, Menthol & Sacharin Sodium was dissolved in ethanol
Pharmaburst, Sodium chloride, Sodium cyclamate Crospovidone were granulated with the Rosuvastatin: GMO suspension and the Povidone solution
The granules were dried and milled.
The milled granules were blended with the remaining excipients to form the final blend for compression.

The tablets prepared by this method achieve 100% dissolution within 5 minutes (Dissolution apparatus II, paddles, 50 rpm, 900 ml, Citrate buffer pH 6.6). The formulation of Table 7 disintegrated within 20-40 seconds of contact with hydrophilic solvent (Basket-rack assembly, Ph. Eur. Method 2.9.1, water at 37° C.). The formulation of Table 8 disintegrated within 40-90 seconds of contact with hydrophilic solvent.

The tablets were administered sublingually to three different human subjects (one Caucasian male, one Caucasian female and one Asian male) and the speed of tablet disintegration monitored. The formulation in Table 7 disintegrated within 20 to 40 seconds of administration for all three subjects. The formulation in Table 8 disintegrated within 40 to 90 seconds of administration for all three subjects.

The manufacturing of tablets involved mixing of Rosuvastatin with the GMO at its melting point for a short period, until a homogenous dispersion was obtained (approximately 5 minutes) and then mixed with other excipients using a high shear mixer. When combined with the other excipients the temperature of GMO returned to below the GMO melting point and the GMO returned to its semi-solid form.

12 mm round tablets of this formulation were stability tested at 5° C. for 6 months. Assay of the 5 mg rosuvastatin showed 100.1% at t=0, 100.4% at t=3 months and 97.9% at t=6 months. The formulation was also stability tested at 25° C./60% RH for 6 months. Assay of the 5 mg rosuvastatin showed 100.1% at t=0, 98.6% at t=3 months and 97.6% at t=6 months. In addition, the assay of the tablets showed 0.05% at t=0, 0.31% at t=3 months and 0.49% at t=6 months of rosuvastatin in the lactone form and 0.3% at t=0, 0.31% at t=3 months and 0.36% at t=6 months of 5-oxo-rosuvastatin calcium (TP-13 impurity 1) at following storage at 25° C./60% RH. The assay of the tablets also showed 0.05% at t=0, 0.08% at t=3 months and 0.05% at t=6 months of rosuvastatin in the lactone form and 0.3% at t=0, 0.23% at t=3 months and 0.24% at t=6 months of the 5-oxo-rosuvastatin calcium at both 3 and 6 months at 5° C.

Example 5—Confirming Formation of Liquid Crystalline Phase

Preparation of Samples Tablets for Simulated Dissolution Study

For equilibrium samples, the tablets were loaded into a transparent polystyrene 96 well plate (Nunc™) and immersed in PBS buffer (pH 6.8). The samples were stored away from light at ambient temperature overnight prior to SAXS experiment.

For the kinetic study of SBT122 and SBT123, 2 tablets were carefully placed in a transparent polystyrene 24 well plate (2 ml per well) to ensure the X-ray beam can transmit through the tablets. The X-ray diffraction patterns were first taken without any solution added. The tablets were then immersed in 2 mL of PBS buffer or saliva donated by the author and other volunteers, the X-ray diffraction patterns were taken overtime, up to 4 hours.

For the kinetic study of SBT177, 2 tablets were disintegrated in PBS using 2 ml vials, the 0.4 ml carefully placed in a transparent polystyrene 96 well plate (0.4 ml per well). The X-ray diffraction patterns were taken overtime, up to 4 hours.

Small Angle x-Ray Scattering (SAXS) Setup

The SAXS/WAXS beamline at Australian Synchrotron, Melbourne, Australia was used to determine the liquid crystalline nanostructure in the samples.

A custom-designed plate holder was used to mount the samples plate directly onto the SAXS/WAXS beamline. Scans were automated using a pre-loaded set of position variables based on the well positions within the plate, the exposure time was 5 seconds. For the kinetic study of SBT177 a single location was tested rather than a full scan of the well.

Data were obtained at ambient temperature (~22° C.). The experiments used a beam of wavelength $\lambda=1.033$ Å (12.0 keV) and a typical flux of $1.2 \times 1013$ photons/s. The 2-D diffraction images were recorded on a Pilatus 1M detector and radially integrated using the in-house software "ScatterBrain".

The liquid crystal phase structures were determined by indexing the Bragg peaks according to their corresponding reflection laws (see Hyde, S. T., Bicontinuous structures in lyotropic liquid crystals and crystalline hyperbolic surfaces. *Current Opinion in Solid State and Materials Science* 1996, 1, 653-662).

Results

TABLE 9

Liquid crystalline structure results

| Tablet | Structure obtained |
| --- | --- |
| SBT122 (1:1) | Pn3m |
| SBT123 (7:1) | Pn3m/Im3m |
|  | Im3m |
| SBT183 (1:1) | Pn3m |
| SBT177 (4:1) | Pn3m |

Example 6—In Vitro Release Testing

Porcine buccal mucosa was freshly isolated from pigs cheeks, mounted between modified Ussing chambers with a donor chamber, receptor chamber and the porcine buccal mucosa in between with a diffusional area of 0.64 cm$^2$, and incubated in Krebs bicarbonate Ringer buffer (KBR, pH 7.4) for 30 min. The mixture or tablet containing rosuvastatin (supplied by Aspen Pharmacare Australia) were applied to the porcine buccal mucosa (ie in the donor chamber) and, when necessary, Parafilm was applied to cover the formulation (ie for tablets and for mixtures containing glyceryl monooleate (GMO) and rosuvastatin). The Parafilm prevented the various formulations from detaching from the buccal mucosa. KBR buffer (1.5 mL) was then added to both the donor and receptor chambers, and receptor samples (200 µL) were collected from the receptor chamber at various time points up to 4-5 hours to determine the amount of rosuvastatin that passed through the porcine buccal mucosa to the receptor chamber. 200 µL of fresh KBR was dispensed into the receptor chamber after each collection (to ensure volume balance). Receptor chamber samples were provided to Aspen Pharmacare Australia for quantification of rosuvastatin by HPLC.

Positive control was tested by making rosuvastatin solutions of 0.4 and 0.8 mg/1.5 ml KBR solution, equivalent to 1:1 and 7:1 ODT's. Total rosuvastatin absorbed per minute in the 1:1 was 0.6 ng/ml and 7:1 was 0.3 ng/ml. Adding more rosuvastatin to the donor chamber didn't improve permeation.

When a mixture was tested, GMO and rosuvastatin were manually mixed on the day of the experiment. The amount of rosuvastatin in the receptor chamber is in FIG. 1. The highest average peak area is in Table 10 below.

TABLE 10 effect of ratio of GMO to API

| Formulation | Highest average peak area result (HPLC) |
| --- | --- |
| GMO:API 1:1 mixture | 22 |
| GMO:API 5:1 mixture | 27 |
| GMO:API 7:1 mixture | 43 |

These results show that including more GMO than API improves permeation of the API through the buccal mucosa.

Figure 2:
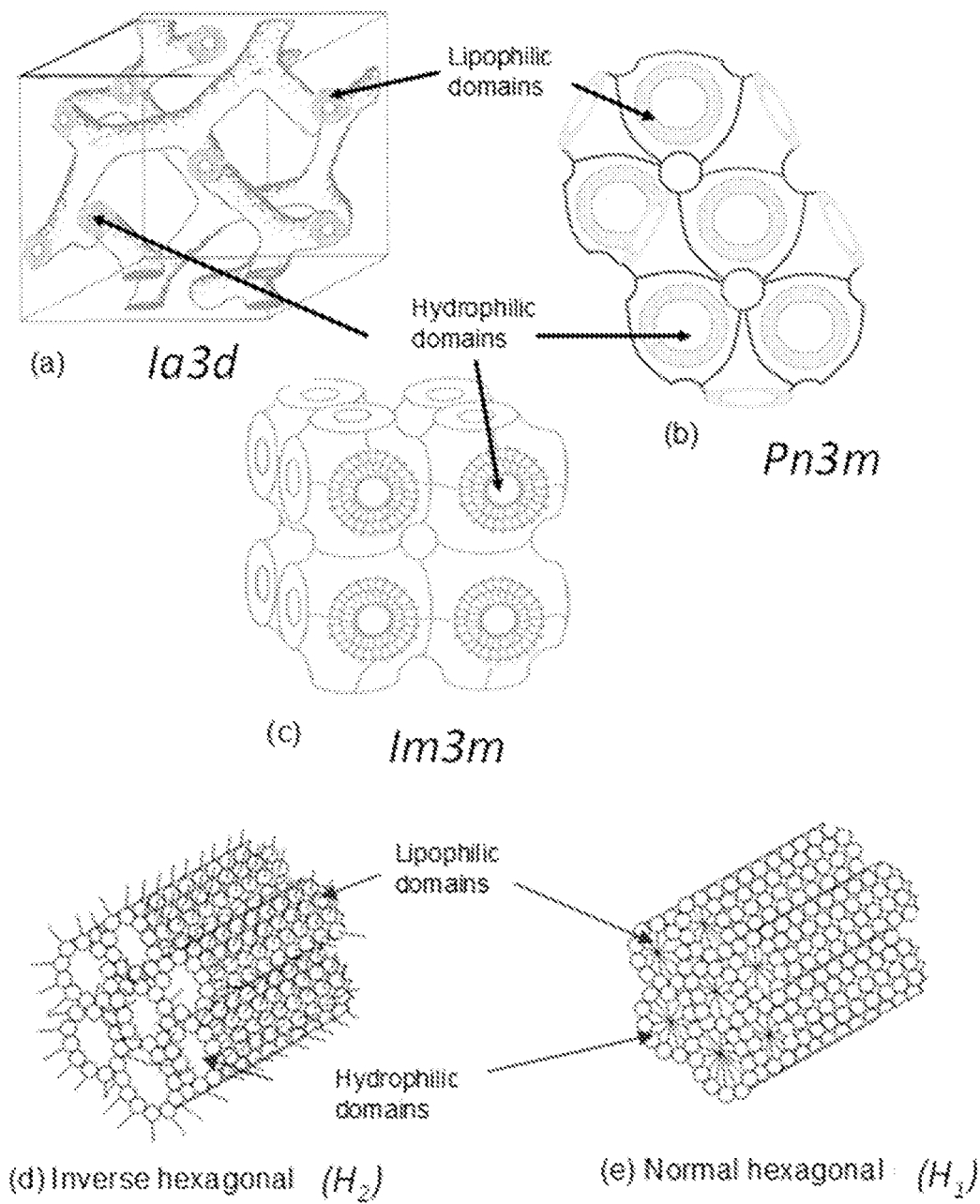
FIG. 2—Diagrammatic representation of the structure of the three main bicontinuous and hexagonal crystal structures where (a) Gyroid (G) Ia3d, (b) Diamond (D) Pn3m and (c) Primitive (P) Im3m. The hexagonal liquid crystals are represented by (d) inverse and (e) normal hexagonal structure. Diagram adapted from Caffrey and Cheng (1995) and Nguyen (2009).

When the tablets were tested, the tablet of Table 5 was applied to the porcine buccal mucosa whole but the tablet of Table 6 was halved before application to the mucosa to better enable the parafilm to hold the tablet in place. The amount of rosuvastatin in the receptor chamber during testing of the tablets is in FIG. 2. The highest average peak area is in Table 11 below.

TABLE 11 effect of tablet formulation

| Formulation | Highest average peak area result (HPLC) |
| --- | --- |
| GMO:API 1:1 mixture | 22 |
| GMO:API 7:1 mixture | 43 |
| Formulation in Table 5 (1:1 ratio) | 93 |
| Formulation in Table 6 (7:1 ratio) | 355 |

These results show that permeation through the buccal mucosa is better with a tablet than with a simple mixture. Also, an increased ratio of GMO to API still improves permeation in the tablet form.

When tested in the permeability cell, SL tablets were well hydrated and disintegrated within the experimental timeframe. 0.17% or 1.34 ng/ml/min of rosuvastatin in the 1:1 SL tablet used in the clinical trial achieving 125-132% (GS & VO) of the oral Crestor tablet, passed into the receiving chamber. Interestingly 1.41% or 6.1 ng/ml/min more of the 7:1 rosuvastatin passed into the receiving chamber. This result was surprising.

Example 7—Clinical Testing of Formulations from Tables 5 and 6

The first study evaluated bioequivalence of 5 mg Crestor and two 5 mg dose forms of the sublingual tablet with equivalent GMO to API (1:1) (SBT122) and 7×GMO to API (7:1) (SBT123). Each participant was given a single dose of medication on separate occasions after appropriate wash-out periods. After single dose of the prescribed preparation, blood samples were collected at time 0, 30 min, 60 min, 2 hours, 4 hours, 6 hours, 8 hours, 24 hours, 36 hours, 48 hours and 72 hours.

Subjects 3 subjects participated in the study. 2 caucasians (1 male and 1 female) and 1 asian male.

Method of Plasma Analysis

Plasma rosuvastatin analysis was undertaken at TetraQ-ADME Bioanalytics of the University of Queensland. The method used is an internal method developed by the University of Queensland to assess bioequivalence of oral rosuvastatin tablets. The method was validated for 1-200 ng/ml rosuvastatin. Plasma rosuvastatin below 1 ng/ml was below the limits of detection and not reported. This method of plasma analysis was based on Martin (2002) and Zhang (2011).

Application of the Method

Subjects fasted overnight and were administered a single dose of rosuvastatin (5 mg Crestor) or the 5 mg oral disintegrating tablet described in Table 5 with 200 ml of water at 8.30-8.45 am. Water was consumed freely and a light snack consumed at 11.30 am.

Plasma was obtained by centrifugation (4,000×g for 10 min at room temperature) of whole blood collected in 4 ml lithium heparin tubes, decanted into 4 ml HDPE cryo-tubes then stored immediately at −180° C. Collected samples were transported within 7 days after freezing of the 72 hour sample collection, and courier overnight to TetraQ in Brisbane, Queensland Australia for analysis.

Results & Discussion

In accordance with literature, the Crestor tablet produced a fast uptake into plasma. The Asian subject produced higher plasma rosuvastatin than the other subjects in the study in accordance with the Crestor prescribing information.

The results are set out in Table 12.

TABLE 12

Clinical results following a single oral 5 mg Crestor, a single 5 mg rosuvastatin 1:1 tablet of Table 5 on the following day and a single 5 mg rosuvastatin 7:1 tablet of Table 6 on the third day

| Subject | % change in total cholesterol | % change in LDL | % change in HDL | % change in Triglycerides |
|---|---|---|---|---|
| Asian male (sublingual dosing) | −12.7% | −22.9 | 14.3 | −16.6 |
| Caucasian female (sublingual dosing) | −17.5% | −21.05 | −5.9 | −37.5 |
| Caucasian male (buccal dosing) | −20.3% | −35.7 | 5.9 | 20.0 |
| Mean | −16.8% | −26.54 | 4.8 | −7.91 |

Figure 3:
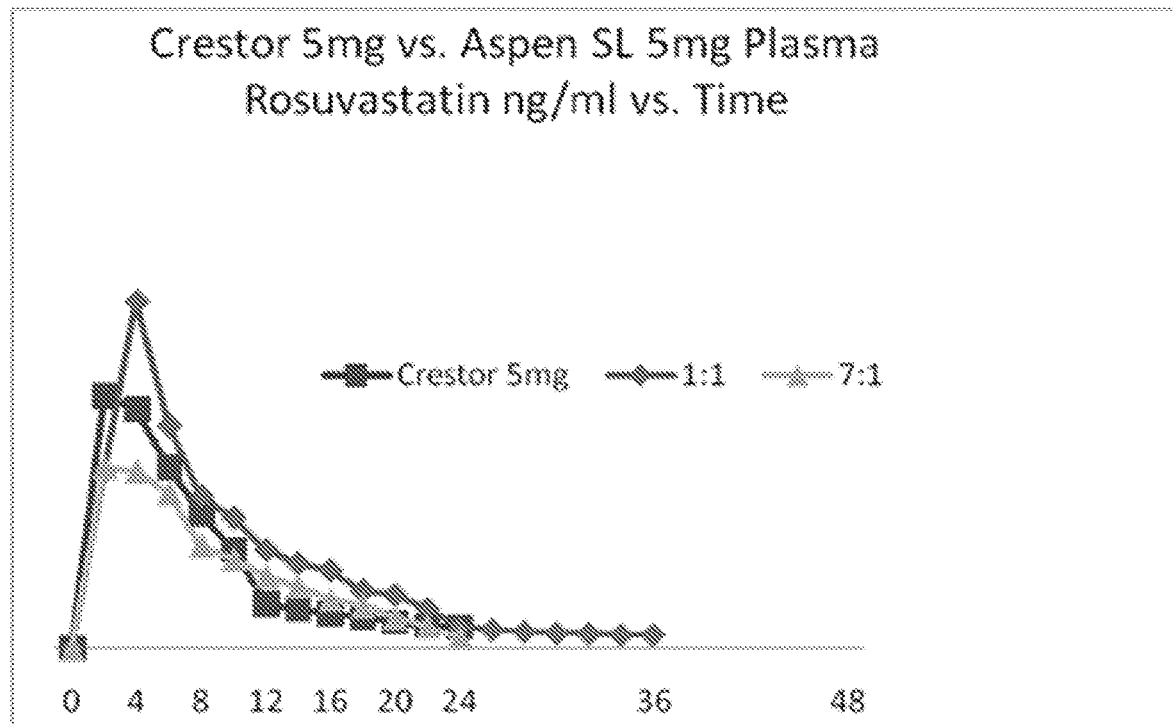
FIG. 3—This figure plots rosuvastatin blood levels following administration of a single dose for each of 5 mg Crestor (oral tablet) (square), 5 mg formulation of Table 5 (diamond) and 5 mg formulation of Table 6 (triangle). This graphs shows the highest ng/ml blood concentration of rosuvastatin was achieved by the formulation of Table 5, followed by Crestor then the formulation of Table 6. The peak blood levels for the formulations of Tables 5 and 6 is at about 4 hours post administration, which is later than the time to peak blood level for Crestor (about 2 hours).
Figure 4:
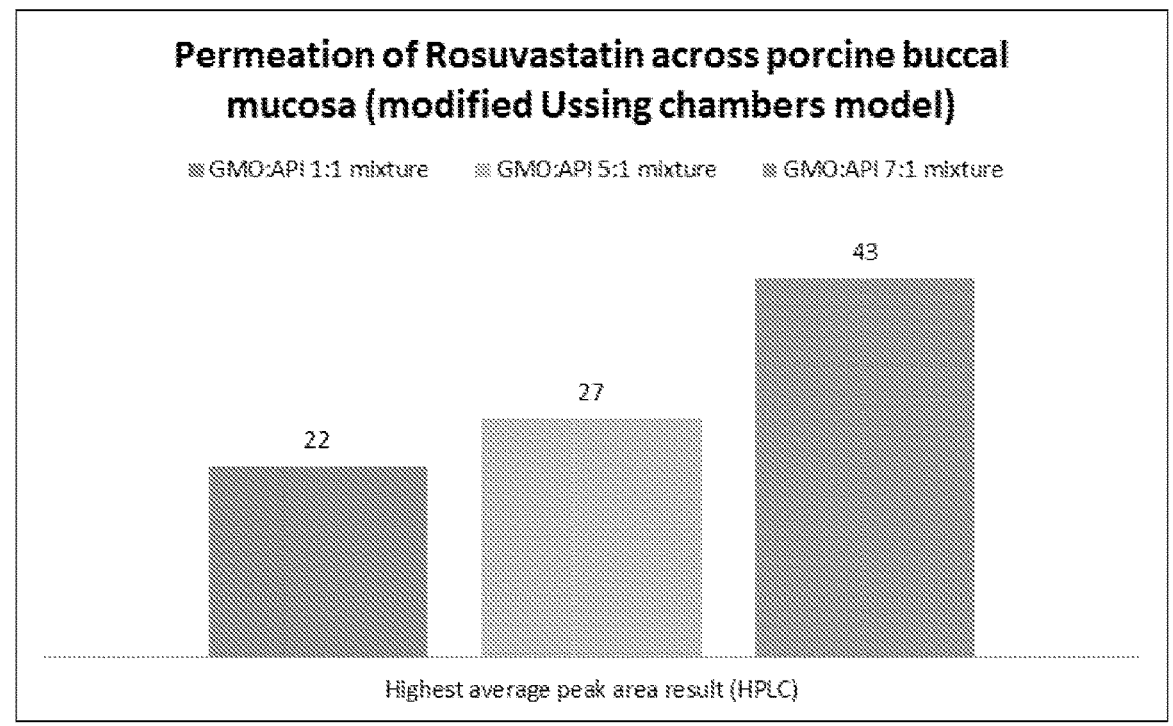
FIG. 4—Shows a bar graph of the highest average peak area result determined by HPLC following the permeation testing described in Example 6. The 7:1 mixture of GMO to rosuvastatin resulted in significantly greater permeation of oral mucosa than the 5:1 mixture, which resulted in greater permeation than the 1:1 mixture. The results suggest greater amounts of GMO result in greater permeation of oral mucosa.
Figure 5:
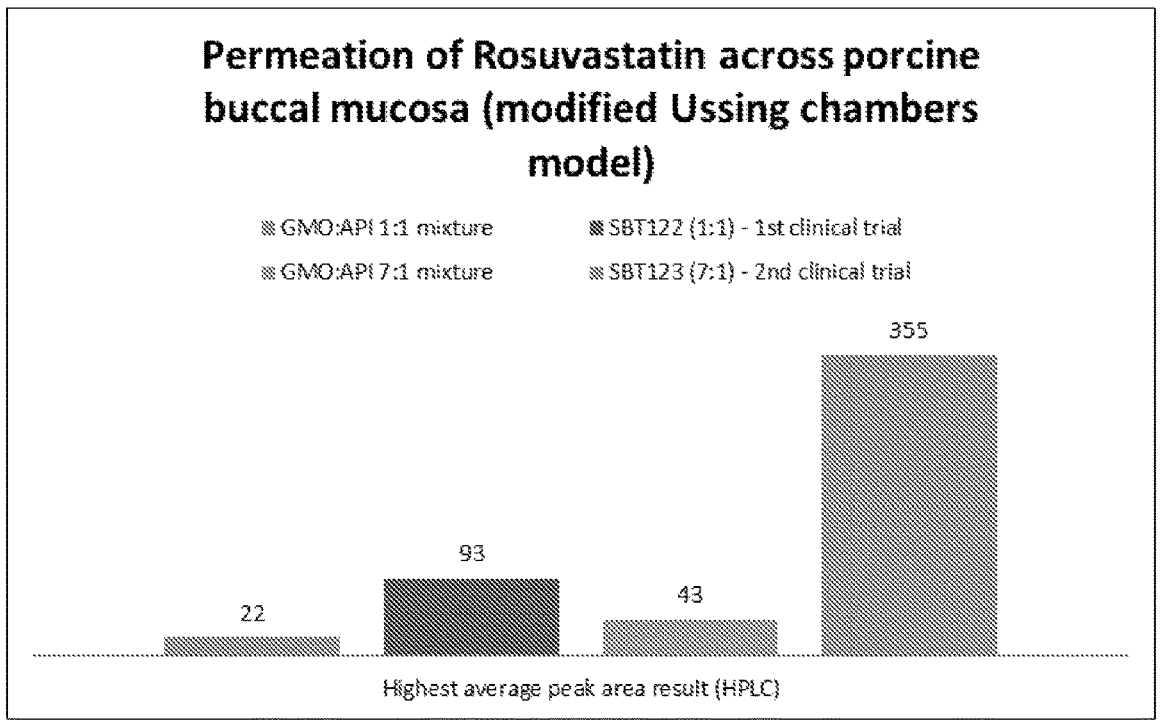
FIG. 5—Shows a bar graph of the highest average peak area result determined by HPLC following the permeation testing described in Example 6. The formulation in Table 5 resulted in greater permeation than the 1:1 GMO to rosuvastatin mixture. This suggests the tablet form assists permeation. The Formulation of Table 6 similarly resulted in greater permeation than the 7:1 mixture of GMO and rosuvastatin.

Both absorption curves for the disintegrating tablets were lower and flatter than the curve for Crestor. FIG. 3 shows a graph of the results. Plasma samples of 12 hours were only taken for the 7:1 product so a predicted value is used for AUC calculation for the 1:1. As oral Crestor was falling steadily no value was inserted for 12 hours.

TABLE 13 peak AUC of each dosage form

| Subject | 5 mg Crestor positive control | 5 mg 1:1 | 5 mg 7:1 |
|---|---|---|---|
| Asian male AUC (sublingual dosing) | 74.67 ng/ml/hr | 127.93 ng/ml/hr (125%) | 54.91 ng/ml/hr (74%) |
| Caucasian female AUC (sublingual dosing) | 52.98 ng/ml/hr | 69.94 ng/ml/hr (132%) | 41.7 ng/ml/hr (79%) |
| Caucasian male AUC (buccal dosing) | 34.8 ng/ml/hr | 34.8 ng/ml/hr (86%) | 14.4 ng/ml/hr (48%) |

*Peak AUC for the formulations of the invention was at about 4 hours while peak AUC for Crestor was at about 2 hours. FIG. 3 shows the peak AUC for each dosage form.

The bucccal absorption may partly explain the lower plasma absorption for the male caucasion subject.

Accordingly, for the subligual tablets the 7:1 is less bioavailable than the Crestor oral but the 1:1 provides higher bioavailability as it is above the 85-120% range accepted by the US FDA. The sublingual absorption may partly explain the higher plasma absorption for the female caucasion subject.

Example 8—Clinical Testing of Redesigned 7:1 ODT (SBT 161)

Disintegration of the 7:1 formulation of Example 6 was investigated after the low AUC results in that testing. Disintegration time was found to be over 45 minutes when taken sublingually and 42 hours plus taken buccally. This disintegration was much slower than the 8-10 min disintegration time for the 1:1 formulation tested in Example 6, which produced higher results. In order to increase the AUC of the 7:1, the tablet was reformulated with a shorter disintegration time (3-5 min).

TABLE 14 formulation of redesigned 7:1 ODT

| Ingredient | % w/w | Function |
|---|---|---|
| Pharmaburst - (co-processed mixture of Mannitol, Sorbitol Crosspovidone & Silicon dioxide) | 77.2 | Filler, Taste masking, Disintegration agent. |
| Rosuvastatin Calcium (micronized) | 1.6 | Drug substance/API |
| Povidone (Poly vinyl pyrrolidone) | 3.2 | Binder |
| Glyceryl Monooleate (GMO) | 10.5 | Bio adhesive/ Mucoadhesive agent, Gelling agent, nonionic surfactant, sustained release agent |
| Sodium Starch Glycolate | 5.0 | Disintegration agent |
| Colloidal Silicon Dioxide | 1.5 | Glidant |
| Magnesium Stearate | 1.0 | Lubricant |
| Ethanol | N/A * | Solvent |

* Evaporated during the drying process.

Process for wet granulation manufacturing:
Rosuvastatin calcium was dispersed in melted GMO
Povidone was dissolved in ethanol
Pharmaburst was granulated with the Rosuvastatin:GMO suspension and the Povidone solution
The granules were dried and milled.
The milled granules were blended with the remaining excipients to form the final blend for compression.

The tablets prepared by this method achieve 100% dissolution in within 15 minutes (Dissolution apparatus II, paddles, 50 rpm, 900 ml, Citrate buffer pH 6.6).

Clinical Testing

The same 3 subjects repeated the pharmacokinetic study but all took the tablet sublingually. The Caucasian male continued taking 1×5 mg ODT sublingually for 4 nights. Lipids were assessed at the conclusion of the study and changes compared to the original study entry point. FBE and total blood analysis was also undertaken for screening purposes to assess other potentially confounding clinical factors.

The results from the conclusion of the study are in Table 15 below.

TABLE 15

AUC results following clinical testing

| Subject | Mean AUC | Mean AUC as % of Oral Crestor |
|---|---|---|
| 5 mg Crestor positive control | 54.15 ng/ml/hr | 100 |
| 5 mg 1:1 (SBT122) | 62.84 ng/ml/hr | 116 |
| 5 mg 7:1 (SBT123) | 38.1 ng/ml/hr | 61 |
| 5 mg 7:1 rapid release (SBT161) | 43 ng/ml/hr | 80 |

The results after the additional 5 days of treatment with sublingual delivery of the 5 mg 7:1 disintegrating tablet are in Table 16 below.

TABLE 16

Cholesterol results

| Lipid | NH&MRC Targets (mmol/L) | Baseline | 5 days 5 mg 7:1 | % Change | % Change after 6 weeks 5 mg oral Crestor* |
|---|---|---|---|---|---|
| Total Cholesterol | <5.6 | 6.2 | 4.6 | ↓28% | ↓24 to 33% |
| LDL | <2.5 | 4.2 | 2.2 | ↓48% | ↓28 to 45% |
| HDL | >1.0 | 1.6 | 2.0 | ↑25% | ↑3 to 13% |

The reductions in LDL-C are surprisingly impressive. An equivalent reduction in LDL from taking 10 mg oral rosuvastatin normally takes at least 6 to 12 weeks and not 9 days. The increase in the HDL is very surprising as statins have traditionally been considered to lower LDL but not increase HDL. Reductions in LDL-C with 10 mg of other statins after 6 weeks therapy are 37% (atorvastatin), 28% (simvastatin) and 20% (pravastatin). The inventors of the present invention are not aware of such a significant reduction in LDL being achieved in such a short time by administration of any statin.

Reductions in LDL-C with 10 mg of other statins after 6 weeks therapy are 37% (atorvastatin), 28% (simvastatin) and 20% (pravastatin).

The reductions in LDL achieved by the sublingual tablets are surprisingly impressive. Efficacy was surprisingly demonstrated after three single 5 mg rosuvastatin doses with total cholesterol (TC) and low density lipoproteins (LDL-C) reducing by 17% and 27%. HDL also slightly increased by 5%. In the second pharmacokinetic study efficacy was reproduced after 5 days of 5 mg ODT. TC reduced by 28% and LDL by 48%. The significant changes in blood lipids with the short term 5 mg ODT are therefore surprising. The reductions have been achieved in 3 to 8 days and not the six weeks or more usually required for similar reductions resulting from administration or oral tablets. The inventors of the present invention are not aware of such a significant reduction in LDL being achieved in such a short time by administration of any statin.

In the second study, with one subject, use of the 5 mg rosuvastatin ODT surprisingly increased HDL by 25% since beginning of the first study (ie the subject conducted the second study following the first study). Interestingly, such changes are only reported in the literature after 6 weeks of daily 10 mg oral dosing. Significant increases in HDL are not usually reported with statins. Even 40 mg oral Crestor reportedly achieves only 10%.

Example 9—Prolonged Release

Figure 6:
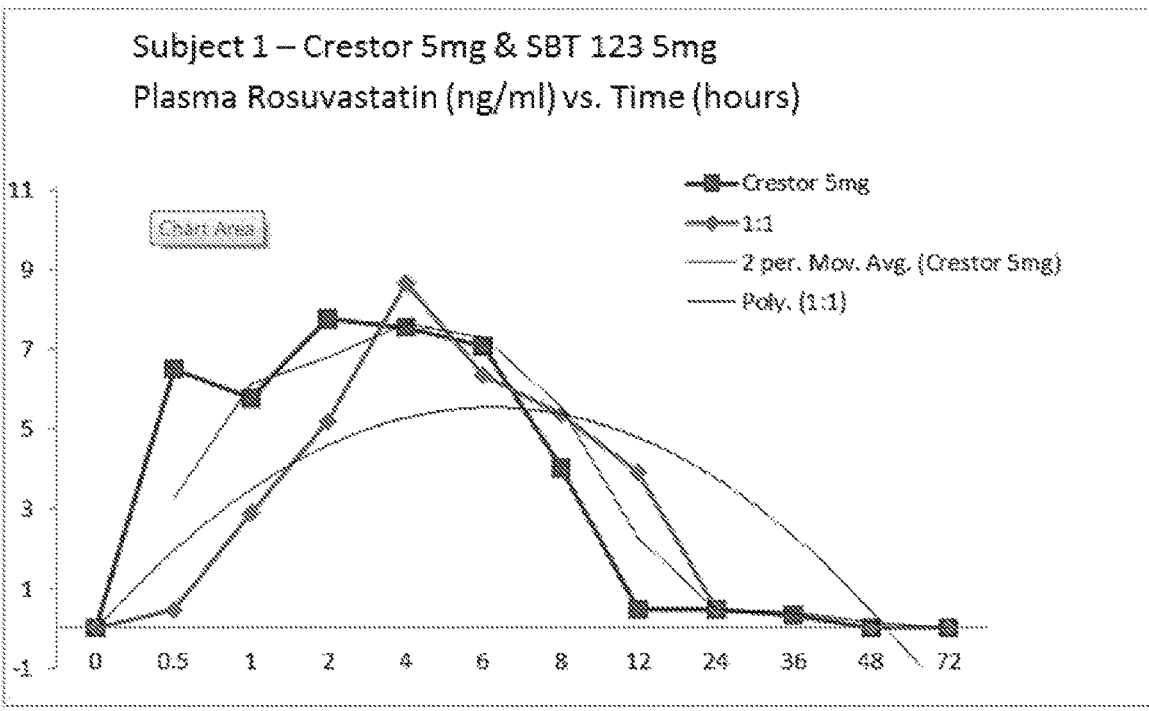
FIG. 6—Graph of the plasma rosuvastatin (ng/ml) v time for a first subject of the clinical study described in Example 7.
Figure 7:
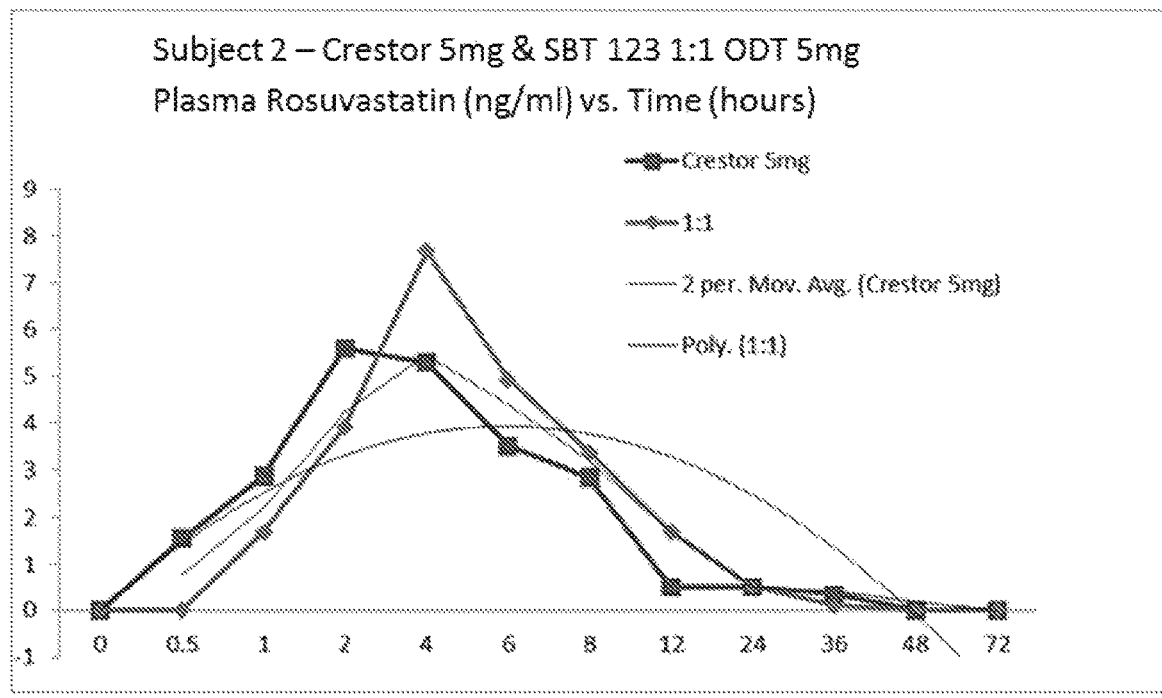
FIG. 7—Graph of the plasma rosuvastatin (ng/ml) v time for a second subject of the clinical study described in Example 7.
Figure 8:
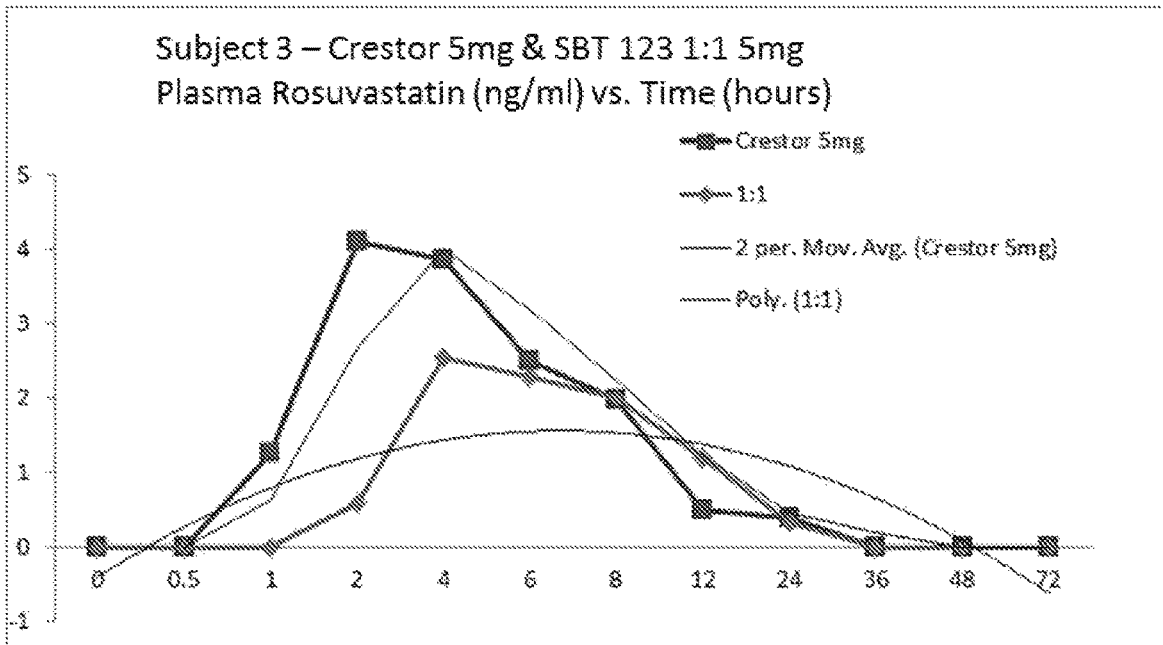
FIG. 8—Graph of the plasma rosuvastatin (ng/ml) v time for a third subject of the clinical study described in Example 7.

FIG. 6 shows the plasma rosuvastatin (ng/ml) v time for 1 subject that received the formulation of Table 5. The results compare plasma rosuvastatin over time when takin oral 5 mg Crestor and the sublingual tablet with equivalent GMO to API (1:1). The moving average curves show a lower and longer curve for the ODT than for the oral tablet. A similar effect was observed for subject 2 (see FIG. 7) and subject 3 (see FIG. 8).

Example 10—Clinical Testing in Patients with Statin Intolerance

A randomised double-blind crossover study was conducted on statin-intolerant subjects.

Methods: 21 subjects (13 males, 18 females, mean age 70, 37-90 yrs) with stable CAD and documented statin-intolerance were recruited. After a 2-week washout period, subjects took blinded sublingual rosuvastatin 5 mg (SBT 176) or placebo for 6 weeks, followed by a 2-week washout period then another 6 weeks of either SL statin/placebo. Blood tests prior to the study, weeks 1, 3 and 6 were obtained and repeated over the next 6-week block. Myalgia scores, creatine kinase (CK) levels, liver function tests (LFT) and TC, LDL and HDL lipid levels were obtained. Myalgia was scored from 0 to 10 using the Visual Analog Scale for Pain, with 0 being "no pain" and 10 being "extreme pain". Statistical analysis was performed on study completion.

Figure 9A:
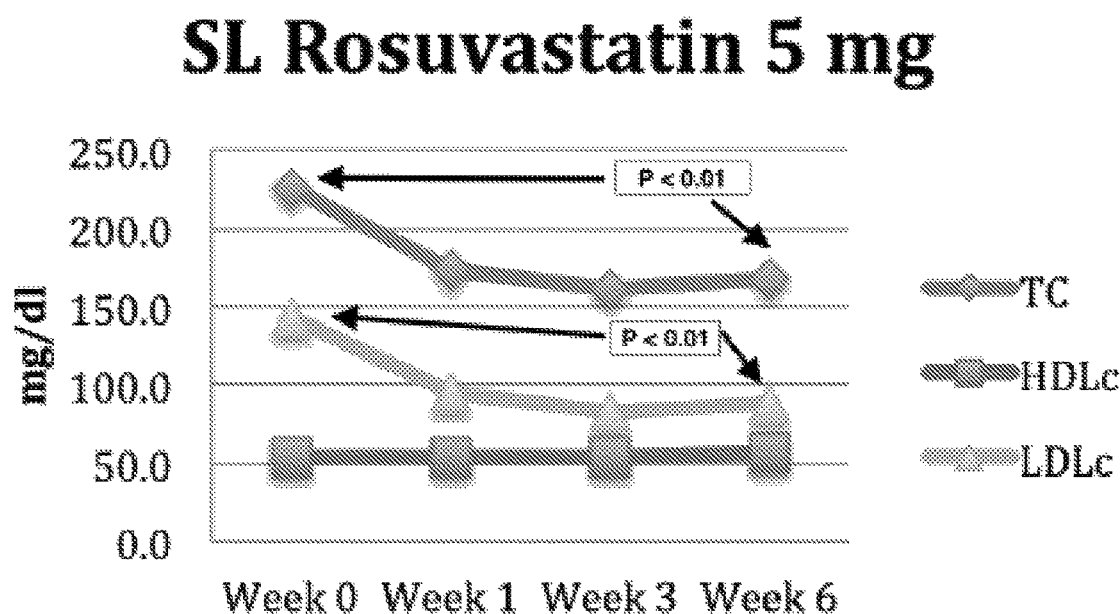
FIGS. 9A & 9B—Graph of the changes in total cholesterol (TC), LDLc and HDLc following clinical testing of fast disintegrating ODT containing rosuvastatin in patients with statin intolerance in Example 10 are in FIG. 9A. The placebo results are in FIG. 9B.
Figure 9B:
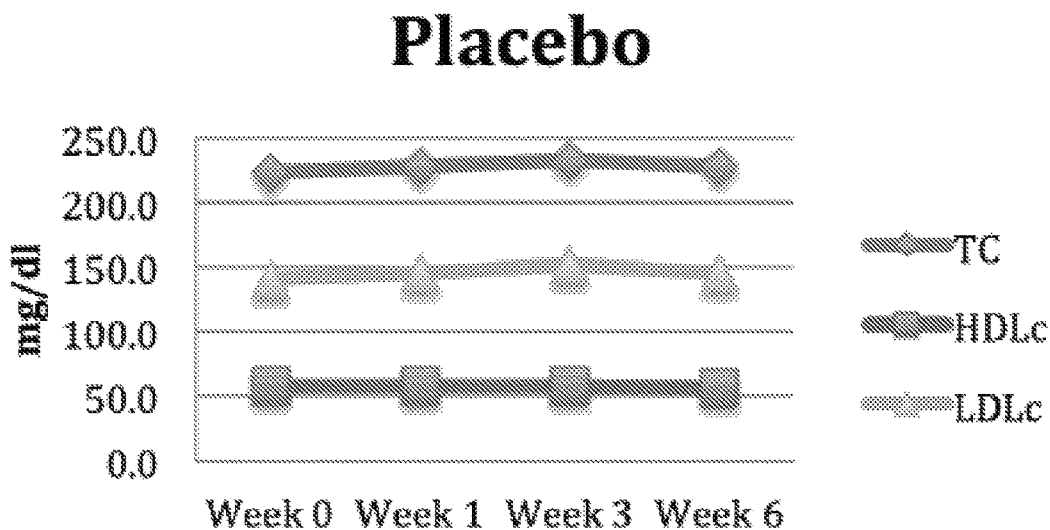

Results: Compared to placebo, there were significant 29% reduction in total cholesterol (p<0.01), 42% reduction in LDLc (p<0.01) and non-significant 6% increase in HDLc (p=0.11), no change in myalgia score (p=0.85). No significant CK change (p=0.83). No change in lipid levels were noted during placebo treatment. Two patients dropped out due to "myalgia", but they were in the placebo group when they dropped out. A graph of the changes in total cholesterol (TC), LLDLc and HDLc is in FIG. 9A and the placebo results in FIG. 9B.

Conclusion: We have successfully demonstrated that a novel sublingual formulation of rosuvastatin may solve the problem of statin-induced myalgia while at the same time effecting significant reduction in cholesterol levels.

Example 11—Transferring Patients from High Dose Traditional Statin Medication A patient taking 80 mg atorvastatin (Lipitor) was selected. The 80 mg atorvastatin dose was ceased and 4 days later the patient commenced SL rosuvastatin (SBT 176). The patient took sublingual rosuvastatin 5 mg for six weeks followed by a two week wash out then placebo for 6 weeks. Blood tests were taken prior to the study, at weeks 1, 3 and 6 and at the end of the placebo period. Myalgia scores, creatine kinase (CK) levels and TC, LDL and HDL lipid levels were obtained. The results are in Table 17 below.

TABLE 17

Results following transition from high dose atorvastatin

|  | Pre-study | Week 1 | Week 3 | Week 6 | Placebo |
|---|---|---|---|---|---|
| TC (mmol/l) | 4.7* | 4.7 | 4.4 | 4.5 | 6.6 |
| HDL | 1.1 | 1.4 | 1.5 | 1.5 | 1.5 |
| LDL | 2.6 | 1.8 | 1.7 | 2.1 | 3.4 |
| CK | 198 | 165 | 126 | 155 | 96 |
| Myalgia Score | 2 | 0 | 0 | 0 | 0 |

When a patient on the highest indicated dose of atorvastatin ceases taking that medication, the patient's total cholesterol (TC) and LDL levels are expected to increase. Similarly, when a patient on the highest indicated dose of atorvastatin ceases taking that medication and commences taking a lower dose of that medication, the patient's total cholesterol (TC) and LDL levels are expected to increase. When the patient taking 80 mg atorvastatin ceased taking that medication and instead took only 5 mg SL rosuvastatin, the patients TC and LDL were expected to increase. Instead, both results were maintained at reasonable levels and an increase in TC and LDL was avoided. Both TC and LDL did rise when the patient subsequently took placebo. The patient's myalgia score lowered as did their CK levels following commencement of the SL treatment.

Example 12—Atorvastatin ODT

A atrovastatin containing ODT was prepared with a formula similar to rosuvastatin ODT SBT176 but using 5.42% w/w of atorvastatin calcium trihydrate and the same amount of GMO. The crospovidone was reduced to 10% w/w and the Pharmaburst increased to 68.21% w/w. The ODT (SBT226) had a 1:1 ratio of GMO to atorvastatin calcium trihydrate and 10 mg atorvastatin calcium trihydrate.

Another atorvastatin ODT (SBT233) containing 10 mg atorvastatin was prepared with a 4:1 ratio of GMO to atorvastatin. The formulation is in Table 18 below.

TABLE 18

ODT with 4:1 GMO to atorvastatin

| Ingredient | % w/w | Function |
|---|---|---|
| Pharmaburst - (co-processed mixture of Mannitol, Sorbitol Crospovidone & Silicon dioxide) | 58.86 | Filler, Taste masking, Disintegration agent. |
| Crospovidone XL | 13.82 | Disintegration agent |
| Sodium Chloride | 0.22 | Osmotic agent |
| Sodium Cyclamate | 0.53 | Sweetener |
| Saccharin Sodium | 0.41 | Sweetener |
| Menthol | 0.21 | Flavouring agent |
| Atorvastatin Calcium Trihydrate | 3.19 | Drug substance/API |
| Povidone (Poly vinyl pyrrolidone) | 2.50 | Binder |
| Glyceryl Monooleate (GMO) | 12.76 | Bio adhesive/Mucoadhesive agent, Gelling agent, nonionic surfactant, sustained release agent |
| Sodium Starch Glycolate | 5.00 | Disintegration agent |
| Colloidal Silicon Dioxide | 1.50 | Glidant |
| Magnesium Stearate | 1.00 | Lubricant |
| Ethanol | N/A * | Solvent |

The method of manufacture was the same as described in Example 4.

Formation of liquid crystalline phase was confirmed for these ODTs and several rosuvastatin ODTs not yet tested using the protocol in Example but having some ODT samples hydrated for 30 min before testing and some for 18 hours before testing. Each sample was tested at 125 times/locations. The results are in table 19 below. The results were the same for the 30 min and 18 hour hydrated samples.

TABLE 19

Liquid crystalline structure results

| API | Batch number | Structure produced - Plate 1: Hydration 18 hrs | Structure produced - Plate 2: Hydration 30 minutes |
|---|---|---|---|
| Atorvastatin 10 mg 1:1 | SBT226 | Double Lamellar | Double Lamellar |
| Atorvastatin 10 mg 4:1 | SBT233 | Double Lamellar | Double Lamellar |
| Rosuvastatin 5 mg 1:1 | SBT176 | Lamellar | Lamellar |
| Rosuvastatin 5 mg 1:1 | SBT187 | Lamellar | Lamellar |
| Rosuvastatin Placebo | SBT189 | Cubic Pn3m | Cubic Pn3m |

*SBT176 was tested when it was over 12 months old. Earlier testing of SBT122, and SBT123, which occurred only a couple months after formulation suggests that SBT176 may have formed form cubic phase if tested closer to its preparation.
SBT 187 has the same formula as SBT 176. SBT 189 is the placebo version of SBT 187.

The permeation of the active ingredient from the atorvastatin containing ODTs of the invention was also tested using a Ussing chamber similar to that of Example 8. This time samples were taken from the receiving chamber of the Ussing chamber repeatedly at 0.5, 1, 1.5, 2, 3 and 4 hours to establish not only that the active ingredient permeated the mucosa but that release of the active ingredient was prolonged.

Figure 10:
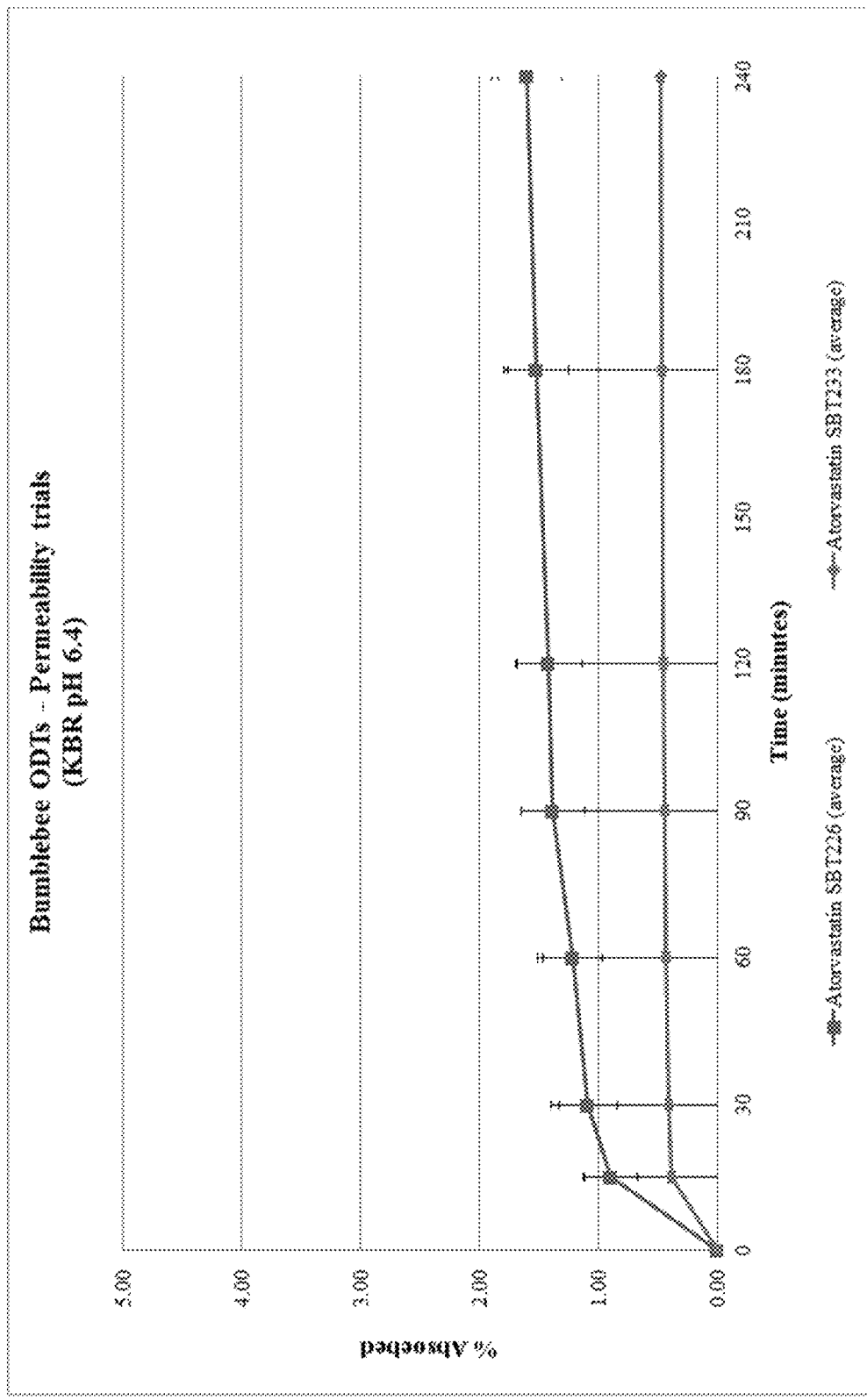
FIG. 10—The appearance of atorvastatin in the receptor chamber over time after application of SBT226 (square) and SBT233 (diamond) to porcine buccal mucosa in the donor chamber of a Ussing chamber. Data are presented as mean±SEM (n=5). Both formulations demonstrate slow release characteristics. SBT226 release the API relatively faster comparing to SBT233 due to lower quantity of GMO.

The appearance of atorvastatin in the receptor chamber over time is depicted in FIG. 10 after application of ODT SBT226 (square) and SBT233 (diamond) to porcine buccal mucosa in the donor chamber of the Ussing chamber. Data are presented as mean±SEM (n=5). Both formulations demonstrate slow release characteristics. SBT226, with a 1:1 ratio of active ingredient to GMO, released the API relatively faster comparing to SBT233, with a 1:4 ratio of active ingredient to GMO. Without being bound by theory, this is thought to be due to the lower quantity of GMO in the SBT226 formulation.

Figure 11A:
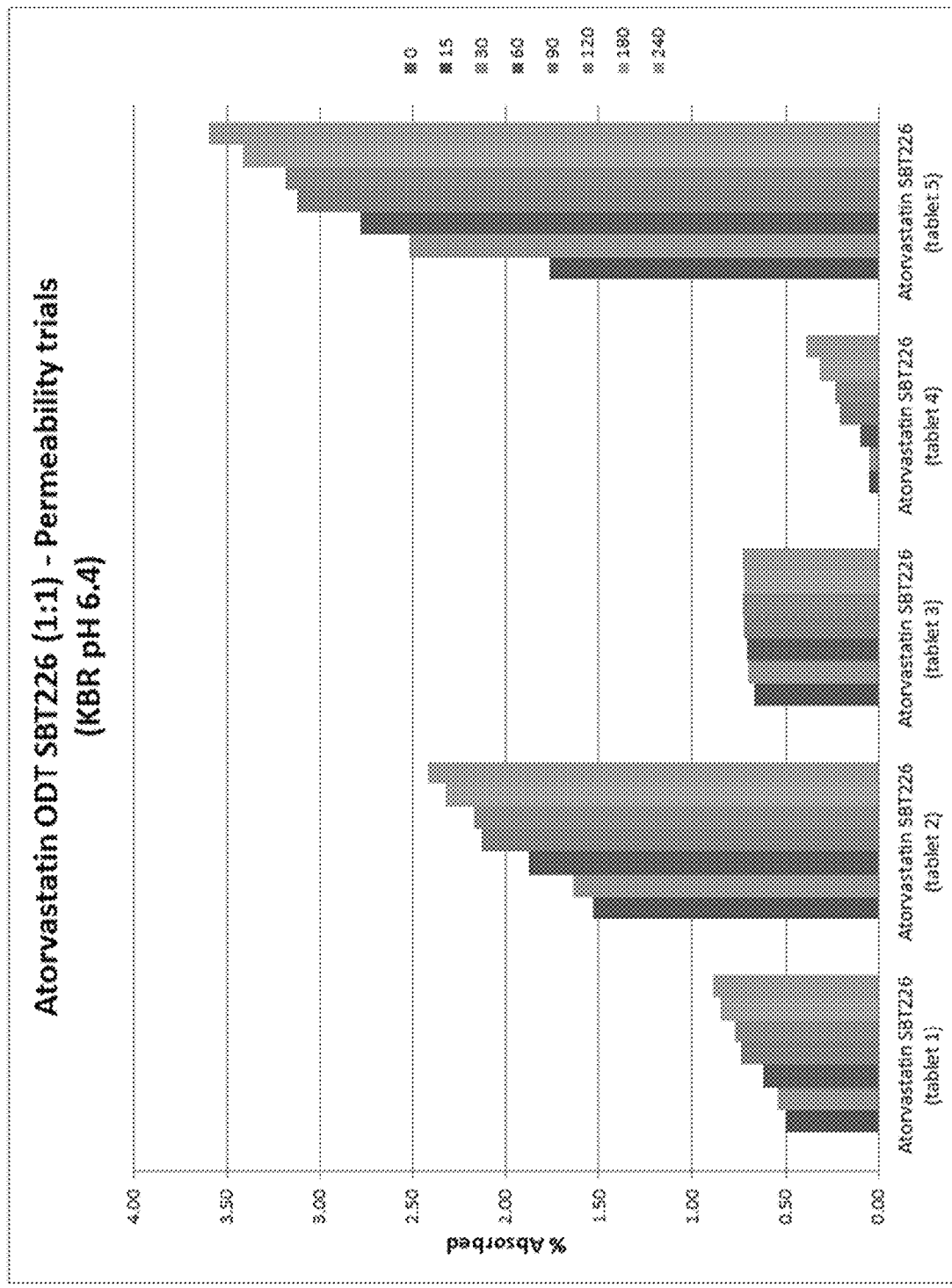
FIGS. 11A & 11B—The results for each individual tablet that were combined to prepare the mean results depicted in FIG. 10 are shown in FIG. 11A—SBT226 tablet testing and FIG. 11B—SBT233 testing. Release of atorvastatin into the receptor chamber at 0, 0.25, 0.5, 1, 1.5, 2, 3 and 4 hours is shown. The individual testing results demonstrate slow release continuing at 4 hours for 4 out of the 5 SBT226 tablets and 3 out of the 5 SBT233 tablets.
Figure 11B:
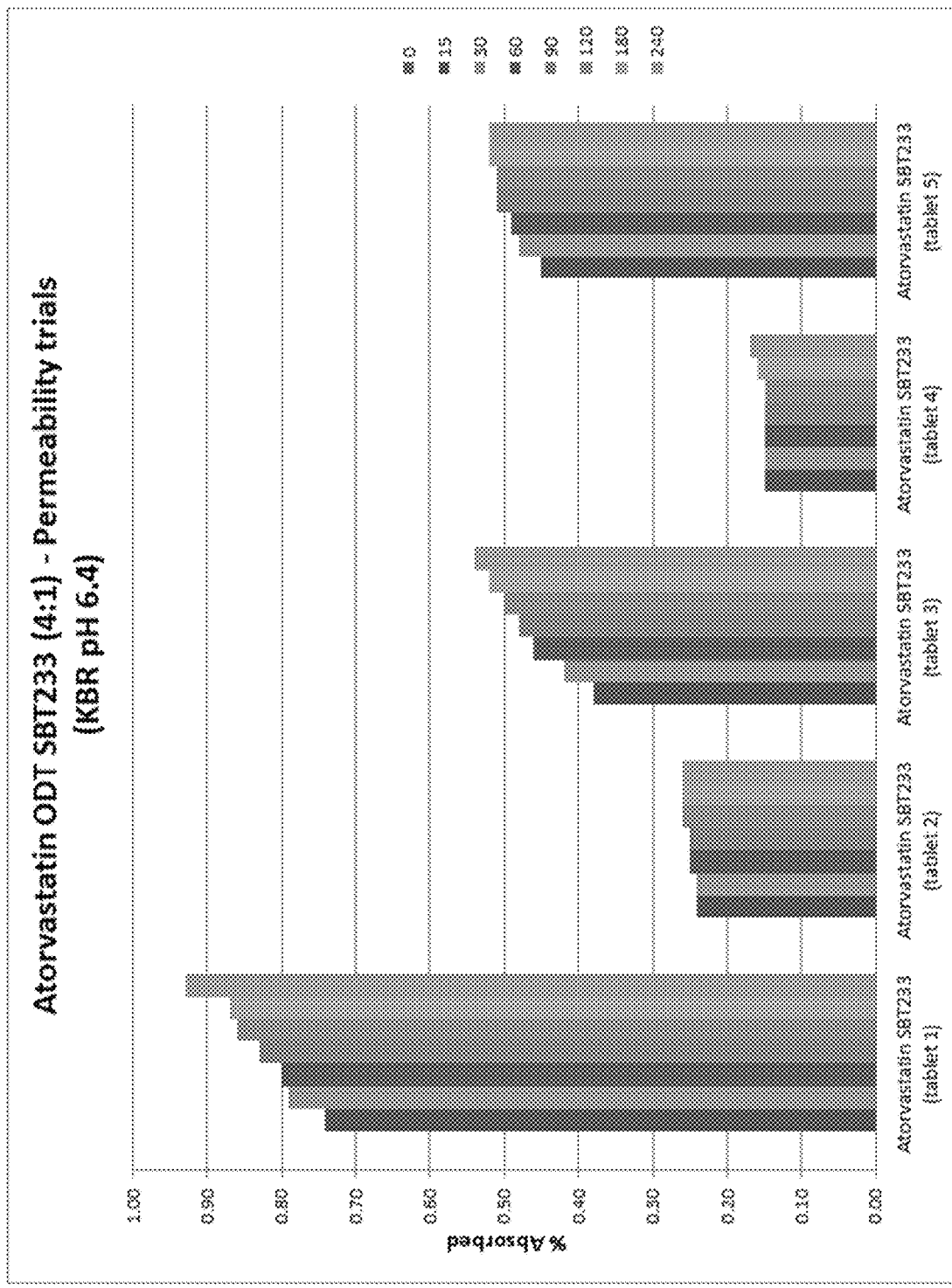

FIGS. 11A and 11B show that in vitro release of atorvastatin through a porcine mucosal membrane was slow release and continuing at 4 hours for 4 of the 5 SBT226 and 3 of the 5 SBT233 tablets tested. Without being bound by theory, Ussing chamber testing is less robust than some in vitro testing methods and it is possible that there was a technical difficulty in the testing of the tablets that did not show slow release. Lipitor oral tablets achieve maximum plasma concentration within 1-2 hours following administration.

The invention claimed is:

1. A method of lowering blood cholesterol levels in a subject in need thereof comprising administering an oral disintegrating tablet (ODT) to the oral mucosa of the subject, wherein the ODT comprises glycerol monooleate in an amount of about 1% to 20% w/w of the ODT and one or more statin compounds in a total amount of 1 to 15% w/w of the ODT, wherein the one or more statin compounds are systemically administered via the oral mucosa, wherein the one or more statin compounds are the sole active ingredients in the ODT, and wherein administering the ODT to the oral mucosa lowers the total blood cholesterol levels in the subject within 7 days.

2. The method of claim 1, wherein the ODT prolongs the release of the one or more statin compounds.

3. The method of claim 1, wherein the administration is sublingual or buccal.

4. The method of claim 1, wherein the method includes treating or preventing the development of dyslipidaemia, cardiovascular disease or atherosclerosis.

5. The method of claim 4, wherein the dyslipidaemia is hyperlipidaemia.

6. The method of claim 1, wherein the subject is identified as in need of blood cholesterol lowering.

7. The method of claim 1, wherein the one or more statin compounds are administered at a total dose of 0.5 to 30 mg/day.

8. The method of claim 1, wherein the method results in a reduction in total cholesterol of about 15% to about 30%.

9. The method of claim 1, wherein the method results in a reduction in LDL-C of about 25% to about 50%.

10. The method of claim 8, wherein the method results in the reduction in total cholesterol within 5 days.

11. The method of claim 1, wherein the ODT retains about 90% or more of the one or more statin compounds following storage at 25° C./60% RH for at least 6 months.

12. The method of claim 1, wherein the w/w ratio of the glycerol monooleate to the active ingredients is about 1:1 to 7:1.

13. The method of claim 1, wherein the self-assembled particles are cubosomes or hexasomes.

14. The method of claim 1, wherein each of the one or more statin compounds is rosuvastatin or atorvastatin.

15. The method of claim 1, wherein the one or more statin compounds are administered at a total dose of 0.5 to 7 mg/day.

16. The method of claim 1, wherein the subject is statin intolerant.

17. The method of claim 16, wherein the statin intolerant subject is a subject with one or more of statin-induced myalgia, statin-induced myositis, and statin-induced myopathy.

18. The method of claim 1, wherein the w/w ratio of the glycerol monooleate to the active ingredients is 10:1 to 1:1.

19. The method of claim 1, wherein the ODT comprises about 1% to about 60% w/w disintegrant.

20. The method of claim 1, wherein the one or more statin compounds are micronized.

* * * * *